United States Patent
Wood et al.

(10) Patent No.: US 8,481,127 B2
(45) Date of Patent: Jul. 9, 2013

(54) CYCLODEXTRIN COMPOSITIONS, ARTICLES, AND METHODS

(75) Inventors: Willard E. Wood, Arden Hills, MN (US); William J. Kuduk, Minneapolis, MN (US); Joseph S. Keute, Blaine, MN (US)

(73) Assignee: Cellresin Technologies, LLC, Bloomington, MN (US)

( * ) Notice: Subject to any disclaimer, the term of this patent is extended or adjusted under 35 U.S.C. 154(b) by 0 days.

(21) Appl. No.: 13/574,287

(22) PCT Filed: Oct. 20, 2011

(86) PCT No.: PCT/US2011/057017
§ 371 (c)(1),
(2), (4) Date: Oct. 11, 2012

(87) PCT Pub. No.: WO2012/134539
PCT Pub. Date: Oct. 4, 2012

(65) Prior Publication Data
US 2013/0029058 A1    Jan. 31, 2013

Related U.S. Application Data

(60) Provisional application No. 61/468,041, filed on Mar. 27, 2011.

(51) Int. Cl.
*C08J 7/18* (2006.01)
(52) U.S. Cl.
USPC .... 427/553; 106/285; 106/287.2; 106/287.23
(58) Field of Classification Search
USPC .................. 427/553; 106/285, 287.2, 287.23
See application file for complete search history.

(56) References Cited

U.S. PATENT DOCUMENTS

| | | |
|---|---|---|
| 3,840,448 A | 10/1974 | Osborn et al. |
| 4,833,674 A | 5/1989 | Takai et al. |
| 4,883,674 A | 11/1989 | Fan |
| 5,518,988 A | 5/1996 | Sisler et al. |
| 5,730,311 A | 3/1998 | Curtis |
| 6,017,849 A | 1/2000 | Daly et al. |
| 6,162,533 A | 12/2000 | Onozawa et al. |
| 6,194,350 B1 | 2/2001 | Sisler |

(Continued)

FOREIGN PATENT DOCUMENTS

| | | |
|---|---|---|
| CN | 1703955 | 12/2005 |
| CN | 101104665 | 1/2008 |

(Continued)

OTHER PUBLICATIONS

Neoh, Tze L. et al., "Dissociation characteristics of the inclusion complex of cyclomaltohexaose (α-cyclodextrin) with 1-methylcyclopropene in response to stepwise rising relative humidity", Carbohydrate Research 345, 2010, 2085-2089.

(Continued)

*Primary Examiner* — Robert S Walters, Jr.
(74) *Attorney, Agent, or Firm* — Pauly, DeVries Smith & Deffner, L.L.C.

(57) ABSTRACT

Cyclodextrin compositions including one or more radiation polymerizable monomers and a cyclodextrin inclusion complex, the cyclodextrin inclusion complex including a cyclodextrin compound and an olefinic inhibitor of an ethylene generation in produce, are coated onto packaging materials and cured. Treated containers and treated package inserts having the cured cyclodextrin compositions are useful in packaging of respiring plant materials.

9 Claims, 5 Drawing Sheets

U.S. PATENT DOCUMENTS

| | | | |
|---|---|---|---|
| 6,313,068 | B1 | 11/2001 | Daly et al. |
| 6,365,549 | B2 | 4/2002 | Sisler |
| 6,548,132 | B1 | 4/2003 | Clarke et al. |
| 6,548,448 | B2 | 4/2003 | Kostansek |
| 6,613,703 | B1 | 9/2003 | Yahiaoui et al. |
| 6,831,116 | B2 | 12/2004 | Bitler et al. |
| 7,169,451 | B2 | 1/2007 | Clarke et al. |
| 7,601,374 | B2 | 10/2009 | Clarke |
| 8,414,989 | B2 | 4/2013 | Wood et al. |
| 2002/0012759 | A1 | 1/2002 | Asayama et al. |
| 2002/0058592 | A1 | 5/2002 | Kostansek |
| 2009/0220739 | A1 | 9/2009 | Chougule |
| 2011/0143004 | A1 | 6/2011 | Wood et al. |
| 2012/0004108 | A1 | 1/2012 | Zhen |
| 2012/0107459 | A1 | 5/2012 | Wood et al. |

FOREIGN PATENT DOCUMENTS

| | | |
|---|---|---|
| CN | 101297659 | 11/2008 |
| CN | 201501603 | 6/2010 |
| CN | 101990937 | 3/2011 |
| CN | 102047946 | 5/2011 |
| CN | 102119719 | 7/2011 |
| DE | 4035378 | 5/1992 |
| EP | 1559746 | 8/2005 |
| EP | 1593306 | 11/2005 |
| GB | 2491424 | 4/2013 |
| WO | WO-2006046254 | 5/2006 |
| WO | WO-2006072180 | 7/2006 |
| WO | WO-2008089140 A1 | 7/2008 |
| WO | WO-2011081877 | 7/2011 |
| WO | WO-2012134539 | 10/2012 |

OTHER PUBLICATIONS

Wooster, Jeffrey J., "Extending the Shelf-life of Fresh-cut Produce (Including the Many Advantages of AFFINITY Polyolefin Plastomers)", The Dow Chemical Company 2010, 1-16.

Ambaw, Alemayehu et al., "Modeling of Diffusion-Adsorption Kinetics of 1-Methylcycloproene (1-MCP) in Apple Fruit and Non-Target Materials in Storage Rooms", 2010, 1-5.

"1-Methylcyclopropene; Amendment to an Exemption from the Requirement of a Tolerance", Federal Register / vol. 73, No. 69 / Wednesday, Apr. 9, 2008 / Rules and Regulations 2008, 19147-19150.

"FAO Specifications and Evaluations for Agricultural Pesticides 1-Methylcyclopropene", 2008, 1-26.

Neoh, Tze L. et al., "Kinetic Study of Thermally Stimulated Dissociation of Inclusion Complex of 1-Methylcyclopropene with α-Cyclodextrin by Thermal Analysis", J. Phys. Chem. B, vol. 112, No. 49, 2008 2008, 15914-15920.

Weerawate, U., "Mathematical Modelling of Active Packaging Systems for Horticultural Products", 2008, 1-363.

Watkins, Christopher B., "Overview of 1-Methylcyclopropene Trials and Uses for Edible Horticultural Crops", 2008, 1-19.

Thoden Van Velzen, E.U., "Packaging for fresh convenience food", Agrotechnology & Food Sciences Group—Wageningenur 2008, 1-29.

Reid, Michael S. et al., "Use of 1-Methylcyclopropene", in Ornamentals: Carnations as a Model System for Understanding Mode of Action HortScience vol. 43(1) Feb. 2008, 95-98.

Nanthachai, Nunchanok et al., "Absorption of 1-MCP by fresh produce", Postharvest Biology and Technology 43 (2007), 291-297.

Neoh, Tze L. et al., "Kinetics of Molecular Encapsulation of 1-Methylcyclopropene into α-Cyclodextrin", Journal of Agricultural and Food Chemistry, vol. 55, No. 26, 2007, 11020-11026.

Hotchkiss, J.H. et al., "Release of 1-Methylcyclopropene from Heat-Pressed Polymer Films", Journal of Food Science—vol. 72, Nr.5, 2007 Section E: Food Engineering & Physical Properties 2007, E330-E334.

Lee, Younsuk S. et al., "Development of a 1-Methylcyclopropene (1-MCP) Sachet Release System", Journal of Food Science—vol. 71, Nr. 1, 2006 Section C: Food Chemistry & Toxicology 2006, C1-C6.

Husken, Debby, "Hydrophilic Segmented Block Copolymers Based on Poly(Ethylene Oxide)", 2006, 1-199.

Watkins, Chris B., "The use of 1-methylcyclopropene (1-MCP) on fruits and vegetables", Biotechnology Advances 24 (2006), 389-409.

Watkins, Chris B. et al., "A summary of physiological processes or disorders in fruits, vegetables and ornamental products that are delayed or decreased, increased, or unaffected by application of 1-methycyclopropene (1-MCP)", 2005, 1-20.

"Conclusion regarding the peer review of the pesticide risk assessment of the active substance 1-methylcyclopropene", EFSA Scientific Report (2005) 30 2005, 1-46.

MacNish, Andrew J. et al., "A simple sustained release device for the ethylene binding inhibitor 1-methylcyclopropene", 2004, 1-50.

Blankenship, Sylvia M. et al., "1-Methylcyclopropene: a review", Postharvest Biology and Technology 28 2003, 1-25.

Sisler, Edward C. et al., "Compounds controlling the ethylene receptor", Bot. Bull. Acad. Sin. (1999) 40: 1_7 http://ejournal.sinica.edu.tw/bbas/content/1999/1/bot41-01.html 1999, 1-13.

Jiang, Yueming et al., "Extension of the shelf life of banana fruit by 1-methylcyclopropene in combination with polyethylene bags", Postharvest Biology and Technology 16 (1999) 1999, 187-193.

Denter, E. et al., "Surface Modification of Synthetic and Natural Fibres by Fixation of Cyclodextrin Derivatives", Journal of Inclusion Phenomena and Molecular Recognition in Chemistry 25, 197-202, 1996, 197-202.

Zhao, Xiao-Bin et al., "Synthesis and charcterization of polymer-immobilized β-cyclodextrin with an inclusion recognition functionality", Elsevier Science B.V., Reactive Polymers 24 (1994) pp. 9-16.

Shkolnik, S. et al., "Radiation-Induced Grafting of Sulfonates on Polyethylene", Journal of Applied Polymer Science, vol. 27, 2189-2196 1982, 2189-2196.

Deeil, J. et al., "1-methylcyclopropene influence 'Empire' and 'Delicious' apple quality during long-term commercial storage", HortTechnology, Jan.-Mar. 2007, 17(1), 46-51.

"Combined Search and Examination Report under Sections 17 and 18(3)", from GB Application No. GB1119545.0, corresponding to U.S. Appl. No. 13/287,944, mailed Jan. 12, 2012, (pp. 1-6).

First Examiner Report Received, for Australia Application No. 2011268471, corresponding to U.S. Appl. No. 61/468,041, mailed Feb. 6, 2012, Including English translation, 1 pg.

Non-Final Office Action, mailed Apr. 27, 2012 in co-pending U.S. Appl. No. 13/287,944, "Cyclodextrin Compositions, Articles, and Methods," (26 pages).

Office Action Received, for United Kingdom Application No. 1119545.0, corresponding to U.S. Appl. No. 61/468,041, mailed Jan. 12, 2012 (pp. 8) Including English translation.

PCT International Search Report and Written Opinion, from International Application No. PCT/US2011/057017, corresponding to U.S. Appl. No. 61/468,041, mailed Jan. 30, 2012, pp. 1-09.

Response to United Kingdom's Office Action, dated Jan. 12, 2012 Filed in the United Kingdom Patent Office on Feb. 13, 2012 for United Kingdom's Patent Application No. 1119545.0 corresponding to U.S. Appl. No. 61/468,041, (pp. 42), 42.

UK Office Action Received, Citation for United Kingdom Application No. 1119545.0, corresponding to U.S. Appl. No. 61/468,041, mailed Apr. 4, 2012 (pp. 7) Including English translation.

Final Office Action, mailed Nov. 8, 2012 in co-pending U.S. Appl. No. 13/287,944, "Cyclodextrin Compositions, Articles, and Methods," (22 pages).

Office action Received, for United Kingdom Application No. 1119545.0, corresponding to U.S. Appl. No. 61/468,041, mailed Sep. 11, 2012 (2 pages).

Notice of Allowance, for U.S. Appl. No. 13/287,944, mailed Feb. 8, 2013 (12 pages).

Combined Search and Exam Report, for United Kingdom Application No. 1218077.4, mailed Oct. 23, 2012 (6 pages).

First Exam Report, for Australian Application 2012203412, mailed Mar. 22, 2013 (3 pages).

Final Office Action, from U.S. Appl. No. 12/967,226, mailed Apr. 26, 2013 (11 pages).

Notice of Allowance, for U.S. Appl. No. 13/287,944, mailed Feb. 8, 2013, 12 pages.

CYCLODEXTRIN COMPOSITIONS, ARTICLES, AND METHODS

This application a claims priority to PCT International Patent Application No. PCT/US2011/057017, filed on Oct. 19, 2011, in the name of CELLRESIN TECHNOLOGIES, LLC, a U.S. national corporation, applicant for the designation of all countries except the U.S., and Inventors Willard E. Wood, a U.S. Citizen, William J. Kuduk, a U.S. Citizen, and Joseph S. Keute, a U.S. Citizen, applicants for the designation of the U.S. only, and claims priority to U.S. Patent Application No. 61/468,041, filed Mar. 27, 2011.

BACKGROUND

The shelf life of produce or produce materials, including whole plants and parts thereof including fruits, vegetables, tubers, bulbs, cut flowers and other active respiring plants or plant materials, is typically determined, at least in part, by the amount of an ethylene hormone generated by the respiring plant material. Ethylene is a known plant ripening or maturation hormone. At any substantial concentration of ethylene in and around the plant material, the maturation of the plant is initiated, maintained or accelerated, depending on concentration. Ethylene-sensitive and -insensitive horticultural commodities (produce and ornamentals) are categorized as being climacteric or non-climacteric on the basis of the pattern of ethylene production and responsiveness to externally added ethylene. Climacteric crops respond to ethylene by an early induction of an increase in respiration and accelerated ripening in a concentration-dependent manner. Non-climacteric crops ripen without ethylene and respiration bursts. However, some non-climacteric crops are sensitive to exogenous ethylene, which can significantly reduce postharvest shelf life. Non-climacteric produce harbor several ethylene receptors which are active. Therefore, exposure of non-climacteric produce to exogenous ethylene can trigger physiological disorders shortening shelf life and quality. See, Burg et al., *Plant Physiol.* (1967) 42 144-152 and generally Fritz et al. U.S. Pat. No. 3,879,188. Many attempts have been made to either remove ethylene from the ambient package atmosphere surrounding the produce or to remove ethylene from the storage environment in an attempt to increase shelf life. Reduced ethylene concentration is understood to be achieved through a decrease in the stimulus of a specific ethylene receptor in plants. Many compounds other than ethylene interact with this receptor: some mimic the action of ethylene; others prevent ethylene from binding and thereby counteract its action.

Many compounds that act as an antagonist or inhibitor block the action of ethylene by binding to the ethylene binding site. These compounds may be used to counteract ethylene action. Unfortunately, they often diffuse from the binding site over a period of several hours leading to a longer term reduction in inhibition. See E. Sisler and C. Wood, *Plant Growth Reg.* 7, 181-191 (1988). Therefore, a problem with such compounds is that exposure must be continuous if the effect is to last for more than a few hours. Cyclopentadiene has been shown to be an effective blocking agent for ethylene binding. See E. Sisler et al., Plant Growth Reg. 9, 157-164 (1990). Methods of combating the ethylene response in plants with diazocyclopentadiene and derivatives thereof are disclosed in U.S. Pat. No. 5,100,462 to Sisler et al. U.S. Pat. No. 5,518,988 to Sister et al. describes the use of cyclopropenes having a $C_{1-4}$ alkyl group to block the action of ethylene.

A suitable olefinic antagonist or inhibitor of receptor sites or ethylene generation in produce is 1-methylcyclopropene, derivatives and analogs thereof have also been tried as an antagonist or inhibitor for the generation of ethylene from respiring plant or produce material. 1-methyl-cyclopropene (1-MCP), 1-butene and other olefins have been shown to have at least some measurable activity for inhibiting ethylene generation and thus extending shelf life. A number of proposals have been made for the method of producing and releasing 1-MCP to inhibit ethylene release and as a result slowing maturation and maintaining the quality of plant materials. Currently 1-MCP is dispensed by the release of 1-MCP from a moisture activated powder or sachet containing complexed 1-MCP. In these technologies, 1-MCP is released from a point source which causes a concentration gradient within the storage chamber thus resulting in a variation in maturation inhibition wherein some produce has an extended life time where other produce exposed to a lesser concentration 1-MCP tends to have less inhibition of ethylene and has a reduced shelf life.

Notwithstanding these efforts, there remains a substantial need in the art for improved plant maturation and degradation prevention. In particular, pressure from worldwide urbanization, manufacturing, and population growth necessitates development of new technologies to increase the efficiency and yield of natural resources expended on delivering food to the growing global population. In the United States, for example, it is estimated that between 8% and 16% of profit loss of fresh produce is due to spoilage and shrinkage which is estimated at $8 billion-$28 billion system wide. This loss translates to significant wasted resources, for example pesticides, fertilizer, and herbicide use; land and water use; transportation, including oil and gas use; and resources associated with the storage of produce. Loss of these and other resources are due to inefficiencies in production and delivery that allows significant spoilage of fruits and vegetables before these critical products can reach the consumer. The United Nations Asian and Pacific Centre for Agricultural Engineering and Machinery's Feasibility Study on the Application of Green Technology for Sustainable Agriculture Development states:

"Technology is a link that connects sustainability with enhanced productivity, where natural resource productivity is efficiently maintained by carefully planning the conservation and exploitation of resources such as soil, water, plants, and animals."

(Feasibility Study on the Application of Green Technology for Sustainable Agriculture Development, United Nations Asian and Centre for Agricultural Engineering and Machinery, at p. 20.) Climate change is raising the stakes for agricultural technology as the world population grows and the amount of arable land shrinks. More mouths to feed, plus less arable land and changing rainfall patterns, means growing demand for technology that lets farmers do more with less. The European Commission recently announced an initiative to optimize food packaging without compromising safety in order to reduce food waste (Harrington, R., "Packaging placed centre stage in European food waste strategy"). The initiative is in response to recent findings that up to 179 kg of food per person is wasted each year. The plan stresses the need for innovation, such as "active packaging" or "intelligent packaging" as one aspect of the solution.

Technology that addresses the issue of fruit and vegetable spoilage is therefore of critical importance as a "green" technology that reduces waste of food and its associated resources by increasing the effective efficiency of arable land.

BRIEF DESCRIPTION OF THE INVENTION

The invention relates to a packaging material including a cyclodextrin composition. The cyclodextrin composition contains an effective amount and a controlled release amount of an olefinic inhibitor of ethylene generation in produce. The packaging material is coated on at least a part of one surface thereof with the cyclodextrin composition. After coating, the cyclodextrin composition is subjected to electromagnetic radiation, such as ultraviolet (UV) radiation, or electron beam (e-beam) radiation. The cyclodextrin composition reacts when exposed to the radiation, such that the composition becomes bonded to the packaging material, or polymerizes to form a polymeric layer or coating on the surface of the packaging material, or a combination of polymerization and bonding. The coated and irradiated packaging material is then used to form containers, packaging, or packaging components or inserts that generate a uniform ethylene inhibiting amount of the olefinic inhibitor, such that live produce stored within the container has a consistent quality and extended useful lifetime. Extending the lifetime of fresh produce can result in significant reduction in food waste. In some cases, packaging material is formed into a container, package, or package component; and then the container, package, or package component is coated with the cyclodextrin composition and irradiated. The irradiated cyclodextrin compositions form a coating or layer on at least a portion of the packaging material or container. The coating or layer contains the cyclodextrin inclusion complex with the olefinic inhibitor compound in the central pore of the cyclodextrin, thereby acting as an effective source of the olefinic inhibitor.

The invention contemplates a treated article that is a treated packaging material or container having an irradiated cyclodextrin composition disposed thereon. The cyclodextrin composition contains an inclusion complex. Within the inclusion complex, cyclodextrin molecules contain an effective amount of the olefinic inhibitor of ethylene generation in produce. The treated packaging material or container is coated with the cyclodextrin composition and the coated packaging material or container is irradiated to form a treated packaging material or container. Treated packaging material is then formed into a flexible, rigid, or semi-rigid container. The treated container releases olefinic inhibitor into an enclosed volume within a packaging structure such that living plant material contained therein has an extended or more useful life time.

The invention contemplates a cyclodextrin composition including one or more radiation polymerizable monomers and a cyclodextrin inclusion complex containing a cyclodextrin and an olefinic inhibitor. The invention also contemplates a cyclodextrin composition including a substituted cyclodextrin compound, wherein the substituted cyclodextrin compound is reactive to electromagnetic irradiation, and wherein some portion of the substituted cyclodextrin compound includes an inclusion complex. The invention also contemplates a radiation cured coating of a cyclodextrin composition such that a cyclodextrin compound or substituted cyclodextrin is bonded to a polymer chain or backbone wherein some portion of the bonded cyclodextrin compound includes an inclusion complex. The invention also contemplates a radiation cured coating of a cyclodextrin composition wherein cyclodextrin and/or cyclodextrin inclusion complexes are not part of the radiation polymerized polymer, but rather are trapped or entangled within the polymerized coating. The invention also contemplates a packaging material having surface functionalization on at least a part of a major surface thereof, wherein the surface functionalization includes a radiation cured cyclodextrin composition.

The invention also contemplates a method of forming an inclusion complex of an olefinic inhibitor with a cyclodextrin to form a cyclodextrin composition, followed by coating the cyclodextrin composition onto a at least part of a major surface of a packaging material or container, and irradiating at least the coated portion of the packaging material or container to form a treated sheet or film.

The invention also contemplates that the treated packaging material or container can be manufactured employing a method whereby the treated packaging material or container is formed under conditions having reduced water content.

The invention also contemplates use of the treated packaging material or container to package respiring produce material. The produce material is enclosed within the packaging material or container and the treated portion of the treated packaging material or container is contacted with an appropriate and activating amount of water such that the cyclodextrin releases the olefinic inhibiting material at sufficient concentration to inhibit produce ripening or maturation. The olefinic inhibitor is also released from the treated packaging material or container by exposure to a controlled level of humidity. During distribution and storage when the packaged produce material storage temperature is low (for example, between about 0° C. to about 14° C.), the humidity in the enclosed volume around the produce will be high (for example, between about 70% to about 100% relative humidity) due to normal water loss from produce respiration into the enclosed package volume. In many cases, the amount of water vapor exceeds the amount that corresponds to 100% relative humidity, and liquid water condenses inside the package. The water vapor and/or liquid water released by the produce within the enclosed volume of the package is sufficient to release the olefinic inhibitor. Alternatively, the internal humidity of the packaging material or container is adjusted by the addition of water prior to sealing the package or container to release the olefinic inhibitor. Relative humidity can be controlled by adding moisture (water mist, spray or steam) to air by humidifiers during packaging.

The invention further contemplates a container or package for produce that is made from conventional packaging materials and contains a package insert comprising a section of a treated sheet or film of the invention that can release the olefinic inhibitor by the increase or addition of a controlled level of humidity.

DETAILED DESCRIPTION

1. Definitions

Figure 1:
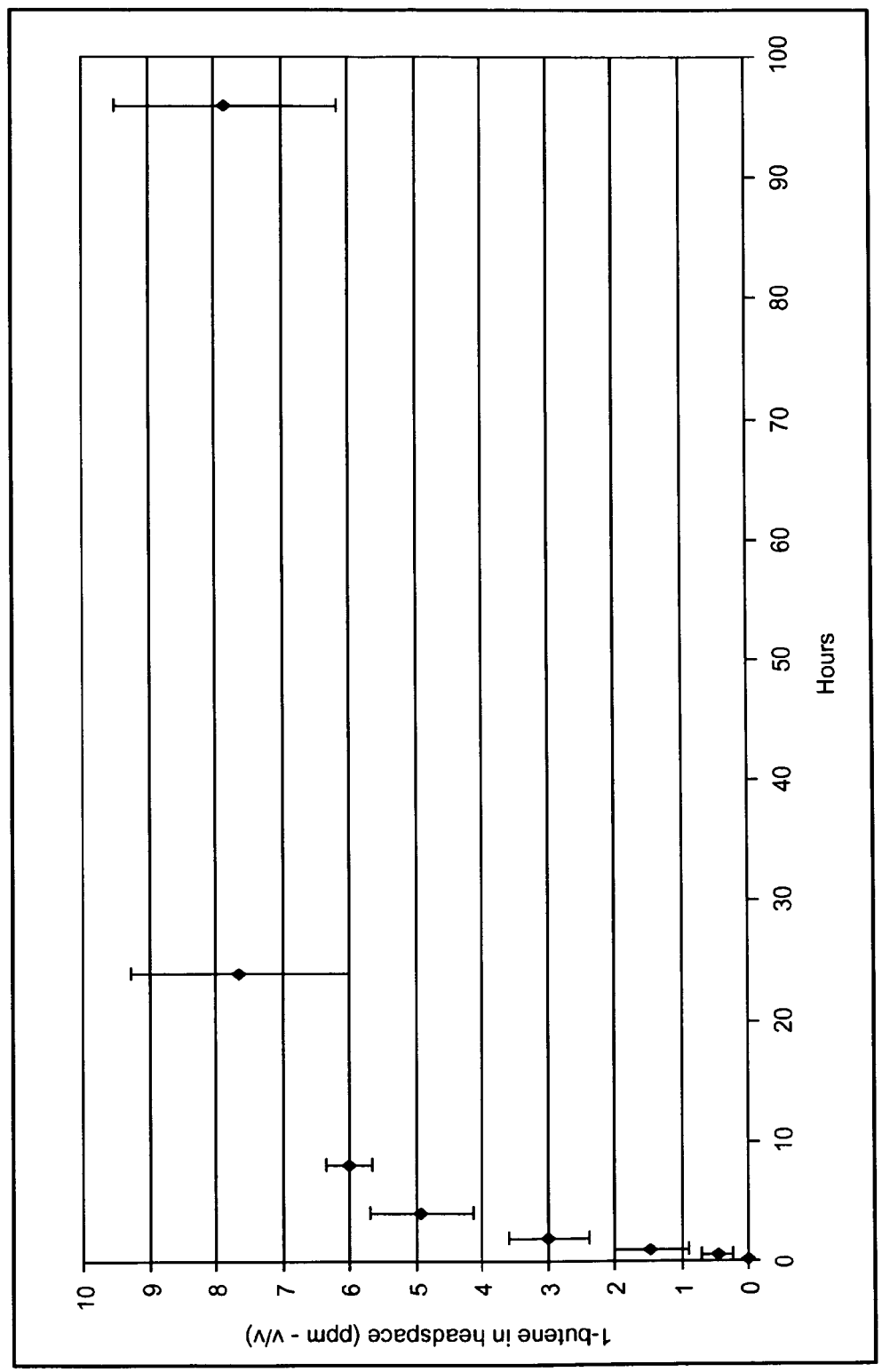
FIG. 1 illustrates headspace concentration of 1-butene as a function of time.

As used herein, the term "cyclodextrin composition" means a composition containing a cyclodextrin inclusion complex that is (1) capable of coating a sheet, film, or container and reacting with UV or e-beam radiation to form a treated sheet, film, or container; or (2) is coated onto a sheet, film, or container; or (3) is a polymerized layer on at least a portion of a major surface of a sheet, film or container; or (4) is covalently bonded to at least a portion of a major surface of a sheet, film or container; or (5) a combination of (3) and (4).

As used herein, the term "cure(d)" or "radiation cure(d)" means to expose a cyclodextrin composition to electromagnetic radiation or electron beam radiation under conditions that cause the composition to undergo a reaction such as polymerization, bonding or grafting to a polymer or a surface, crosslinking, or a combination thereof. Electromagnetic radiation includes, but is not limited to, ultraviolet (UV) radiation, microwave radiation, and gamma radiation. "Radiation polymerizable" or "radiation curable" monomers and crosslinkers are compounds that are polymerized or crosslinked as a result of interaction with electromagnetic radiation or electron beam radiation. In some embodiments, radiation polymerizable monomers and crosslinkers are also polymerizable by thermal means.

As used herein, the term "cyclodextrin" or "cyclodextrin compound" means a cyclomalto-oligosaccharide having at least five glucopyranose units joined by an $\alpha(1-4)$ linkage. Examples of useful cyclodextrins include $\alpha$-, $\beta$-, or $\gamma$-cyclodextrin wherein $\alpha$-cyclodextrin has six glucose residues; $\beta$-cyclodextrin has seven glucose residues, and $\beta$-cyclodextrin has eight glucose residues. Cyclodextrin molecules are characterized by a rigid, truncated conical molecular structure having a hollow interior, or pore, of specific volume. "Cyclodextrin" can also include cyclodextrin derivatives as defined below, or a blend of one or more cyclodextrins. The following table recites properties of $\alpha$-, $\beta$-, and $\gamma$-cyclodextrin.

| CYCLODEXTRIN TYPICAL PROPERTIES | | | |
|---|---|---|---|
| CD PROPERTIES | $\alpha$-CD | $\beta$-CD | $\gamma$-CD |
| Degree of polymerization (n =) | 6 | 7 | 8 |
| Molecular Size (A°) | | | |
| inside diameter | 5.7 | 7.8 | 9.5 |
| outside diameter | 13.7 | 15.3 | 16.9 |
| height | 7.0 | 7.0 | 7.0 |
| Specific Rotation $[\alpha]^{25}_D$ | +150.5 | +162.5 | +177.4 |
| Color of iodine complex | Blue | Yellow | Yellowish Brown |
| Solubility in Distilled water (g/100 mL) 25° C. | 14.50 | 1.85 | 23.20 |

As used herein, the term "cyclodextrin inclusion complex" means the combination of an olefinic inhibitor compound and a cyclodextrin wherein the olefinic inhibitor compound is disposed substantially within the pore of the cyclodextrin ring. The complexed olefinic inhibitor compound must satisfy the size criterion of fitting at least partially into the cyclodextrin internal cavity or pore, to form an inclusion complex. The cyclodextrin inclusion complexes include, inherent to the formation and existence of the inclusion complex, some amount of "uncomplexed" cyclodextrin; this is because (1) in embodiments synthesis of the inclusion complex does not result in 100% formation of inclusion complex; and (2) in embodiments, the inclusion complex is in equilibrium with uncomplexed cyclodextrin/uncomplexed olefinic inhibitor. Each combination of cyclodextrin and olefinic inhibitor has a characteristic equilibrium associated with the cyclodextrin inclusion complex.

As used herein, the term "cyclodextrin derivative" or "functionalized cyclodextrin" means a cyclodextrin having a functional group bonded to one of the cyclodextrin glucose moiety hydroxyl groups. One example is a group that causes the cyclodextrin derivative to be soluble in a radiation polymerizable monomer. Some cyclodextrin derivatives are described, for example, in U.S. Pat. No. 6,709,746.

As used herein, the term "olefinic inhibitor", "olefinic inhibitor compound" or "olefinic inhibitor of ethylene generation" is intended to mean an olefinic compound that contains at least one olefinic double bond, has from about 3 to about 20 carbon atoms and can be aliphatic or cyclic having at least minimal ethylene antagonist or inhibition activity.

As used herein, the term "packaging material" means any component of packaging in which produce is contained or which is exposed to the enclosed volume within a produce bag or container. Packaging material includes, for example, sheets or films from which a package for enclosing produce is made, or any package made for enclosing produce, or any material used on or inside a package. Packaging material includes, for example, thermoplastic packaging films and foils, and wrapping or bags formed therefrom; coated or uncoated paper webs and sheets as well as bags or cardboard boxes; thermoformed punnets; wax or film coatings applied directly to the produce or to a container; multilayer packaging constructions; printed coatings, embossed indicia, labels placed on or in packaging or on produce, adhesives used to close or seal packaging or adhere labels and the like thereto; ink printed directly on produce, directly on packaging, or on a label that is then adhered to packaging; and the like. In embodiments, one or more packaging materials employed in a package includes a cyclodextrin composition of the invention.

As used herein, the term "treated packaging material" means a packaging material or container that has disposed on at least a portion of a major surface thereof a cyclodextrin composition and wherein the cyclodextrin composition has further been cured.

As used herein, the term "treated package insert" means a piece or section of a treated packaging material that is inserted into a produce package or into some other container defining an enclosed volume.

As used herein, the term "treated laminate" or "treated laminated packaging material" means a cyclodextrin composition or cured cyclodextrin composition combined with and disposed between on one surface of a first packaging material and one surface of a second packaging material, wherein the first and second packaging materials are the same or different. In general, treated packaging materials include treated laminated packaging materials.

As used herein, the term "treated container" or "treated package" means (1) packaging material that has been formed into a flexible, semi-rigid, or rigid container or package to enclose produce, then coated with a cyclodextrin composition and cured; or (2) a treated packaging material that has been formed into a flexible, semi-rigid, or rigid container or package. Treated containers include bags, boxes, cartons, punnets, and other such containers used to package produce material. In conjunction with its intended use and for some period of time, the treated container will include an enclosed volume. Thus, the treated container will be closed or sealed to contain an enclosed volume; or will be included within an enclosed volume.

As used herein, the term "treated laminated container" means (1) a first packaging material that has been formed into a flexible, semi-rigid, or rigid container to enclose produce, wherein a cured cyclodextrin composition is combined with and disposed between on one surface of a first packaging material and one surface of a second packaging material, wherein the first and second packaging materials are the same or different; or (2) a first packaging material that has been formed into a flexible, semi-rigid, or rigid container to enclose produce, wherein a cyclodextrin composition is combined with and disposed between one surface of the container and a second layer of a packaging material that is the same or different from the first packaging material, and then the cyclodextrin composition is cured; or (3) a treated laminated packaging material that has been formed into a flexible, semi-rigid, or rigid container. In general, treated containers include treated laminated containers.

As used herein, the term "permeable" as applied to a packaging material, a cured cyclodextrin composition, a treated packaging material, a treated container, a treated laminated packaging material, or a treated laminated container means that the material, container, or composition has a permeability to the olefinic inhibitor of equal to or greater than 0.01 ($cm^3 \cdot mm/m^2 \cdot 24$ hrs·bar) at standard temperature and pressure (STP) and 0% relative humidity; or permeability to water vapor of equal to or greater than 0.1 ($g \cdot mm/m^2 \cdot 24$ hr) at 38° C. and 90% relative humidity, when measured according to ASTM D96; or permeability to $O_2$ of equal to or greater than 0.1 ($cm^3 \cdot mm/m^2 \cdot 24$ hr·bar) at 23° C. and 0% relative humidity, when measured according to ASTM D3985; or permeability to $CO_2$ of equal to or greater than 0.1 ($cm^3 \cdot mm/m^2 \cdot 24$ hr·bar) at 23° C. and 0% relative humidity, when measured according to ASTM D1434; or a combination thereof. As used herein, the term "impermeable" as applied to a packaging material, a cured cyclodextrin composition, a treated packaging material, a treated container, a treated laminated packaging material, or a treated laminated container means that the material, container, or composition has a permeability to the olefinic inhibitor of less than 0.01 ($cm^3 \cdot mm/m^2 \cdot 24$ hrs·bar) at STP and 0% relative humidity; or permeability to water vapor of less than 0.1 ($g \cdot mm/m^2 \cdot 24$ hr) at 38° C. and 90% relative humidity, when measured according to ASTM D96; or permeability to $O_2$ of less than 0.1 ($cm^3 \cdot mm/m^2 \cdot 24$ hr·bar) at 23° C. and 0% relative humidity, when measured according to ASTM D3985; or permeability to $CO_2$ of less than 0.1 ($cm^3 \cdot mm/m^2 \cdot 24$ hr·bar) at 23° C. and 0% relative humidity, when measured according to ASTM D1434; or a combination thereof.

The term "produce" or "produce material" includes any whole plant, plant part, such as a fruit, flower, cut flower, seed, bulb, cutting, root, leaf, flower, or other material that is actively respiring and, as a part of its maturation, generates ethylene as a maturation hormone (climacteric) or ripens without ethylene and respiration bursts (non-climacteric).

2. Compositions, Articles, and Methods of Making

We have found that one or more cyclodextrin compounds are useful to form a cyclodextrin composition using mild conditions. The cyclodextrin compositions are useful to form a coating on at least a portion of a major surface of one or more packaging material or containers. After coating a cyclodextrin composition on at least a portion of a surface of a packaging material or container, the coated surface is irradiated with UV or e-beam radiation to form a treated sheet, film, or container. In some embodiments the treated packaging material is used to form a container. In other embodiments the treated packaging material is used to form a treated package insert, wherein a section of the treated packaging material is attached to or simply inserted into a produce container. The treated container, or a container having a treated package insert disposed within its interior, is used to package produce.

Using the compositions, articles, and methods of the invention enables olefinic inhibitor compounds to be employed in a safe, convenient, and scalable manner that avoids subjecting the cyclodextrin inclusion complex to harsh conditions that can cause loss of the olefinic inhibitor from the cyclodextrin inclusion complex. Further, the treated packaging material, containers, and package inserts of the invention impart low but constant levels of olefinic inhibitor release therefrom when disposed within an enclosed volume in the presence of water vapor and thus provide long term inhibition of ripening or maturation of the produce while disposed inside the enclosed volume.

The cyclodextrin compositions of the invention include at least a cyclodextrin inclusion complex and a monomer. In embodiments, the cyclodextrin inclusion complex is simply admixed with the monomer at the desired ratio to form the cyclodextrin composition.

The cyclodextrin employed to form the cyclodextrin inclusion complex is selected for the specific volume of the cyclodextrin pore. That is, the cyclodextrin pore size is selected to fit the molecule size of the olefinic inhibitor. The olefinic inhibitor is a compound having from 3 to about 20 carbon atoms, comprising at least one olefinic bond and comprising a cyclic, olefinic or diazo-diene structure. Examples of compounds useful as the olefinic inhibitor of ethylene generation include 1-methyl cyclopropene, 1-butene, 2-butene, and isobutylene. Of these, 1-methyl cyclopropene, or 1-MCP has been found to be particularly useful. It has been found that 1-MCP has a molecular size that is suitable for formation of an inclusion complex when combined with α-cyclodextrin, or α-CD. In embodiments, the inclusion complex contains about 0.10 to 0.99 mole of the olefinic inhibitor per mole of cyclodextrin, or about 0.20 to 0.95 mole of the olefinic inhibitor per mole of cyclodextrin, or about 0.30 to 0.90 mole of the olefinic inhibitor per mole of cyclodextrin, or about 0.50 to 0.90 mole of the olefinic inhibitor per mole of cyclodextrin, or about 0.50 to 0.80 mole of the olefinic inhibitor per mole of cyclodextrin, or about 0.30 to 0.70 mole of the olefinic inhibitor per mole of cyclodextrin.

Methods of forming cyclodextrin inclusion complexes are known and are described, for example, in U.S. Pat. Nos. 6,017,849 and 6,548,448 as well as in Neoh, T. Z. et al., *J. Agric. Food Chem.* 2007, 55, 11020-11026. Typically the cyclodextrin and the olefinic inhibitor are mixed together in a solution for a period of time sufficient to form the inclusion complex. In the case of 1-MCP and α-cyclodextrin, α-cyclodextrin is dissolved in water and 1-MCP is bubbled into the solution for a period of time at room temperature. The inclusion complex precipitates from the solution as it forms and thus is easily isolated by simple filtration followed by vacuum drying. The dried cyclodextrin inclusion complex is then ready for use. Storage in a dry container with minimal head space is sufficient.

In some embodiments, the cyclodextrin inclusion complex is formed with a cyclodextrin derivative. Cyclodextrin derivatives are employed to form the inclusion complex in some embodiments to improve miscibility in the cyclodextrin composition. Cyclodextrin derivatives employed to improve miscibility of the cyclodextrin composition include any of the cyclodextrin derivatives described in U.S. Pat. No. 6,709,746 or in Croft, A. P. and Bartsch, R. A., *Tetrahedron* Vol. 39, No. 9, pp. 1417-1474 (1983). In some embodiments where a cyclodextrin derivative is employed to form the cyclodextrin inclusion complex, the olefinic inhibitor is introduced in a non-water solvent, for example a hydrocarbon having 1 to 10 carbons, an alcohol having 1 to 10 carbons, a heterocyclic or aromatic solvent having 4 to 10 carbons. In some such embodiments, blends of one or more solvents are employed. In other embodiments, the inclusion complex is formed prior to functionalization of the cyclodextrin derivative. In such embodiments, care must be taken during the functionalization to employ techniques and select functional group chemistries that avoid displacing the olefinic inhibitor from the inclusion complex, for example by preferential inclusion of one of the compounds employed in the functionalization.

Monomers useful in forming the cyclodextrin compositions include any of the known compounds having one or more unsaturated bonds that are polymerizable by free radical polymerization methods or plasma polymerization methods such as electron beam radiation polymerization. In embodiments, useful vinyl monomers include acrylates, methacrylates, acrylamides, allylic monomers, α-olefins, butadiene, styrene and styrene derivatives, acrylonitrile, and the like. Some examples of useful monomers include acrylic acid, methacrylic acid, and alkyl esters of acrylic or methacrylic acid wherein the ester groups have between 1 and 18 carbons, in some embodiments between 1 and 8 carbons, and are linear, branched, or cyclic. In embodiments, blends of two or more monomers are employed in the cyclodextrin compositions. In some such embodiments, one or more monomers are selected for improved wetting, adhesion, or both of the cyclodextrin composition to the target substrate. In some such embodiments, one or more monomers are selected to provide specific permeability properties. In some embodiments, monomers are selected to provide a targeted permeability of the cured cyclodextrin composition to water, or to the olefinic inhibitor, or both. Careful control of permeability is selected for optimum controlled release of the olefinic inhibitor during use. Various additional components, as are described below, are further selected to control olefinic inhibitor release properties and other physical properties of the cured cyclodextrin compositions of the invention.

In some embodiments, monomers having more than one unsaturated and polymerizable bond are employed in the cyclodextrin compositions, for example diacrylates such as ethylene glycol diacrylate, hexanediol diacrylate, and tripropyleneglycol diacrylate; triacrylates such as glycerol triacrylate and trimethylolpropane triacrylate; and tetraacrylates such as erythritol tetraacrylate and pentaerythritol tetraacrylate; divinyl benzene and derivatives thereof; and the like. Such monomers provide crosslinking to the cured cyclodextrin composition. Other compounds that are useful monomers where UV polymerization is employed include photoactive crosslinking agents. Photoactive crosslinking agents include, for example, benzaldehyde, acetaldehyde, anthraquinone, substituted anthraquinones, various benzophenone-type compounds and certain chromophore-substituted vinylhalomethyl-s-triazines, such as 2,4-bis(trichloromethyl)-6-p-methoxystyryl-s-triazine. In some such embodiments, a monomer having more than one unsaturated and polymerizable bond, or a photoactive crosslinker, is present at less than about 10% by weight of the cyclodextrin composition, for example at about 0.1% to 5% by weight of the cyclodextrin composition. In embodiments, the monomer or blend of monomers is a liquid at the temperature at which the cyclodextrin composition is coated onto a thermoplastic sheet, film, or container. In some embodiments, the cyclodextrin, the cyclodextrin inclusion complex, or both are miscible in the monomer or monomer blend.

The cyclodextrin composition is an admixture of the cyclodextrin inclusion complex and one or more monomers, and optionally one or more crosslinking agents, along with any additional components desirably included in the cyclodextrin composition. In embodiments, the amount cyclodextrin inclusion complex employed in the cyclodextrin composition is about 0.001% by weight to 25% by weight of the composition, or about 0.01% by weight to 10% by weight of the composition, or about 0.05% by weight to 5% by weight of the composition. The amount of cyclodextrin inclusion complex included in a particular formulation is selected based on the amount of olefinic inhibitor desired in the enclosed space within the treated container, in conjunction with variables such as the permeability of the coating to water and the olefinic inhibitor. Criteria informing this selection are described in greater detail below.

In embodiments, one or more additional components are added to the cyclodextrin composition. Adhesion promoters, antifouling agents, thermal or oxidative stabilizers, colorants, adjuvants, plasticizers, and small amounts of solvents are examples of additional materials that are added to the cyclodextrin compositions in some embodiments. In some embodiments, the cyclodextrin composition includes a polymerization initiator. In some embodiments where curing is carried out by UV radiation, it is desirable to include a photoinitiator that will absorb the UV radiation and become activated, thereby initiating the polymerization of the unsaturated polymerizable monomer(s) and any other components of the cyclodextrin composition that contain UV polymerizable moieties. In many embodiments, a photoinitiator is selected based on the wavelength of UV radiation to be employed. Where a photoinitiator is employed, it is included in the cyclodextrin compositions at about 0.01% by weight to 5% by weight based on the weight of the cyclodextrin composition, for example 0.5% by weight to 2% by weight based on the weight of the cyclodextrin composition. Examples of suitable photoinitiators include those sold under the trade name IRGACURE® by Ciba Specialty Chemicals Corp. of Tarrytown, N.Y.; those sold under the trade name CHEMCURE® by Sun Chemical Company of Tokyo, Japan; and LUCIRIN® TPO sold by BASF Corporation of Charlotte, N.C.

In some embodiments, an additional component is a prepolymer. Prepolymers are either formed in situ from the cyclodextrin composition by prepolymerization thereof, optionally followed by addition of more monomer and photoinitiator, or are added to the cyclodextrin composition in order to increase coating viscosity of the composition prior to curing. Prepolymerization is a bulk or continuous polymerization method wherein a minor amount of polymerization, for example 1% to 10%, of the bulk coating composition is carried out to achieve a target viscosity. The prepolymers are of any suitable molecular weight and are soluble in the monomer or monomers of the cyclodextrin composition. Prepolymers are formed in situ or added to the cyclodextrin composition at any amount that is useful to provide the target coating viscosity. In a typical prepolymerization, a cyclodextrin composition is subjected to UV radiation in bulk or continuous mode until the desired viscosity is reached, forming a prepolymerized cyclodextrin composition. In some embodiments, targeted viscosities for the prepolymerized cyclodextrin compositions are from about 10 cP to 2000 cP, or about 100 cP to 1000 cP. In embodiments, one or more additional monomers, crosslinkers, initiators, or a combination thereof are then added to the prepolymerized cyclodextrin composition. The prepolymerized cyclodextrin composition is then coated and cured, wherein the viscosity of the prepolymerized cyclodextrin composition allows a thicker layer to be coated than would be practicable using the cyclodextrin composition without prepolymerization. In embodiments, coatings 25 microns and thicker of prepolymerized cyclodextrin composition are formed, for example between about 25 microns and 100 microns. Such coating thicknesses are useful, for example, where the cured cyclodextrin composition is a pressure-sensitive adhesive. In some embodiments, the cyclodextrin inclusion complex is added to the coating composition after prepolymerization; however, in many embodiments the cyclodextrin inclusion complex is added prior to prepolymerization because mixing of the components is more easily accomplished prior to forming a higher viscosity composition.

In some embodiments, an additional component is a water scavenger. A water scavenger is a compound that is soluble or dispersible in the coating composition to be cured, and is available to react preferentially with water molecules such that it effectively acts to scavenge ambient moisture from airborne humidity during standard processing conditions. The amount of water scavenger added should be a minimum amount to react with ambient moisture during processing. This is because, in the envisioned packaging applications wherein the cyclodextrin compositions are included in a produce container, water is required to facilitate release of the olefinic inhibitor into the container. Thus, an amount of water scavenger should be provided in the cyclodextrin composition that is quickly depleted once a substantial amount of water vapor is encountered. Examples of water scavengers suitably employed in the cyclodextrin compositions of the invention include various orthoesters and hexamethyldisilazane. In embodiments, about 1 wt % or less based on the total cyclodextrin composition weight of the water scavenger is added to the cyclodextrin compositions, for example about 0.01 wt % to 1 wt % based on the total cyclodextrin composition weight or about 0.05 wt % to 0.5 wt % based on the total cyclodextrin composition weight.

In some embodiments, an additional component is a desiccant. In the present invention, desiccants are employed to scavenge water from the interior of an enclosed volume into which a respiring produce material is expected to generate an excess of the desired amount of water. The effects of excess water are described in more detail below. Desiccants are also added, in some embodiments, directly to the interior of a treated container or treated laminated container of the invention separately from the cyclodextrin composition itself; however, in some embodiments, the desiccant is added directly into the cyclodextrin composition for convenience and/or efficiency. Suitable desiccant materials include, for example, silica gel and molecular sieve type desiccants. The amount of desiccant incorporated within a cyclodextrin composition or cured cyclodextrin composition is not particularly limited and is selected based on the particular end use, that is, the type of package, volume of enclosed space, type of produce to be packaged, and the like. In general, the amount of desiccant is selected to be about 0.001 wt % to 99 wt % based on the total weight of the cyclodextrin composition, or about 0.1 wt % to 50 wt % based on the total weight of the cyclodextrin composition, or about 1 wt % to 10 wt % based on the total weight of the cyclodextrin composition.

The packaging materials that are suitably coated with a cyclodextrin composition on at least a portion thereof include any packaging material that is suitable for surface coating followed by curing with UV or e-beam radiation. Suitable packaging materials include paper and cardboard and other natural and synthetic biomass-based packaging materials, as well as synthetic petroleum-based thermoplastic polymeric films, sheets, fibers, or woven or nonwoven fabrics that are useful as packaging materials for produce, and composite materials including one or more thereof. Some examples of packaging materials usefully employed to form containers, labels, laminates (i.e. treated laminated packaging materials) or package inserts include paper, cardboard, coated paper or cardboard such as extrusion coated paper or cardboard, chipboard, nonwoven or woven fabrics, wood/thermoplastic composites, polyvinyl halides such as poly(vinyl chloride) (plasticized and unplasticized) and copolymers thereof; polyvinylidene halides such as polyvinylidene chloride and copolymers thereof; polyolefins such as polyethylene, polypropylene, and copolymers and morphological variations thereof including LLDPE, LDPE, HDPE, UHMWPE, metallocene polymerized polypropylene, and the like; polyesters such as polyethylene terephthalate (PET) or polylactic acid (PLA) and plasticized variations thereof; polystyrene and copolymers thereof including HIPS; polyvinyl alcohol and copolymers thereof; copolymers of ethylene and vinyl acetate; and the like. Blends, alloys, crosslinked versions thereof, and composites thereof are also useful in various embodiments. Two or more layers of such packaging materials are present in some embodiments as multilayer films or carton constructions.

The packaging materials contain, in some embodiments, one or more fillers, stabilizers, colorants, and the like. In some embodiments the packaging materials have one or more surface coatings thereon. In some embodiments the packaging material has a surface coating thereon prior to coating the cyclodextrin composition. Surface coatings include protective coatings such as wax, acrylic polymer coatings, and the like; coatings to render surfaces printable; coatings to render otherwise permeable packaging materials impermeable; adhesive coatings; primers; tie layer coatings; metalized or reflective coatings; and the like. The type and function of surface coatings are not particularly limited within the scope of the invention; likewise the manner in which the surface coatings are applied is not particularly limited. In various embodiments where a surface coating will be exposed to the enclosed volume within a produce package, the surface coating is subsequently coated with the cyclodextrin composition.

In one such commercially important embodiment, commercial growers and distributors commonly use polyethylene extrusion coated recyclable paperboard or carton board packaging to ship produce. The polyethylene coating provides water resistance and water vapor protection in the generally moist and humid environments that are typical of shipping and storage conditions for fresh fruits and vegetables. Printed paperboard packaging can range from bulk bins to specialized display cartons. Printed indicia are, in some embodiments, embossed indicia. The extrusion coated surface provides an opportunity to include a cyclodextrin composition of the invention.

In some embodiments the packaging material is treated with a plasma or corona treatment prior to coating the cyclodextrin composition. Such surface treatments are well known in the industry and are often employed in the industry to modify the surface energy of packaging materials, for example to improve wetting or adhesion of coatings or printed materials to the surface of a packaging material. Such surface treatments are likewise useful in some embodiments to improve wetting and adhesion of the cyclodextrin compositions to the packaging material.

In some embodiments, the packaging material is treated with a primer prior to coating the cyclodextrin composition. In some such embodiments films and sheets of thermoplastics used as packaging materials are obtained already pre-coated with a primer; a wide variety of such films and sheets are available in the industry and are targeted for improving adhesion of various types of coatings thereto. In some embodiments a plain film or sheet is coated "in line" with a primer designed to improve adhesion of radiation polymerizable coatings prior to coating the cyclodextrin composition. A plethora of such coatings and technologies are available and one of skill will understand that primer coatings are optimized for each coating formulation and each film or sheet type. Some examples of primer compositions suitably disposed between the packaging material surface and the cyclodextrin compositions of the invention include polyethyleneimine polymers such as polyethyleneimine, alkyl-modified polyethyleneimines in which the alkyl has 1 to 12 carbon atoms, poly(ethyleneimineurea), ethyleneimine adducts of polyaminepolyamides, and epichlorohydrin adducts of polyaminepolyamides, acrylic ester polymers such as acrylamide/acrylic ester copolymers, acrylamide/acrylic ester/methacrylic ester copolymers, polyacrylamide derivatives, acrylic ester polymers containing oxazoline groups, and poly (acrylic ester)s. In embodiments, the primer composition is an acrylic resin, a polyurethane resin, or mixture thereof. In embodiments the primer composition includes at least one radiation curable polymer, oligomer, macromonomer, monomer, or mixture of one or more thereof.

In some embodiments the packaging material is a sheet or film that is formed into a container suitable to enclose produce within an enclosed space. In other embodiments the packaging material is a sheet or film that is converted into coupons, strips, tabs, and the like for the purpose of insertion into the enclosed space defined by an otherwise untreated produce container. In some embodiments the coupons, strips, tabs, and the like are labels that are adhesively applied to the produce or the container. In some such embodiments, the coupons, strips, tabs, and the like are labels that are further printed with one or more indicia. In embodiments, the indicia are embossed indicia. The cyclodextrin composition is present, in various embodiments, on any surface that is directly or indirectly exposed to the enclosed space. In some embodiments, the packaging material is a treated laminate. In some embodiments the treated laminate is permeable to the olefinic inhibitor on a first side thereof and is impermeable to the olefinic inhibitor on a second side thereof. In some embodiments, the packaging material is a treated laminate that is permeable to water on at least a first side thereof.

Containers suitable to enclose produce within an enclosed space include, for example, bags, boxes, cartons, pallets, and punnets. In some embodiments, the package is designed to contain a single item of produce, such as a bag to contain a banana or a head of lettuce; in other embodiments, the package is a carton to contain multiple items, such as a carton to contain a bushel of apples or several pints of berries; in still other embodiments, the container is designed to enclose a pallet of smaller produce boxes or punnets, such as large polyethylene bags that enclose a pallet of berries for transport. In still other embodiments, the container is a truck, boat, or plane wherein a sealed and/or controlled environment is provided for transport of produce.

In many embodiments, more than one packaging material is employed in forming a container; in such embodiments the cyclodextrin composition is present on one or more packaging component. In an illustrative example, a semi-rigid polypropylene container is filled with produce and then sealed with a polyvinyl chloride film. The produce includes a paper label attached to the produce. Within the container is a polyester pouch or cup containing a sauce, dressing, or other condiment. The pouch or cup has indicia printed thereon. In this example, the cyclodextrin composition is present on all or a portion of an inner surface of the container or the film, an outer surface of the cup or pouch or the paper label, and/or included in the ink that is printed on the cup or pouch. Alternatively, the cyclodextrin composition is included on a package insert or label that is separately added to the container prior to sealing with the film. In some embodiments, a combination of more than one such surface includes the cyclodextrin composition. In yet another illustrative example, a polyethylene extrusion coated paperboard carton is coated or printed on a surface thereof with a cyclodextrin composition, followed by curing. The paperboard carton is then filled with produce, stacked on a pallet with a plurality of other cartons, and the pallet is enclosed in a polyethylene bag. In some embodiments, all of the cartons include the cured cyclodextrin composition; in other embodiments, only one or some percent of the cartons include the cured cyclodextrin composition. In some examples of this technology, the bag further contains a controlled atmosphere or a modified atmosphere, or is a selectively permeable membrane material. Such atmosphere variations and permeable membrane materials are discussed in detail below. In some embodiments, the bag further contains a desiccant in a pouch or sachet.

In yet another representative example, a plastic bag containing produce is a treated laminated container, that is, the cured cyclodextrin composition does not directly contact the interior of the container. The cyclodextrin composition is cured directly on a first packaging material with a second packaging material applied on top of the cyclodextrin composition and cured after lamination to form a treated laminate; the treated laminate is then formed into a bag. The packaging material that forms the exterior of the bag is impermeable to the olefinic inhibitor. The packaging material contacting the interior of the bag is permeable to at least the olefinic inhibitor. At least one of the packaging materials is permeable to water vapor. In a related example, the treated laminate is a film for wrapping e.g. a carton or other container for produce material. In another related example, the cyclodextrin composition is cured directly on a first packaging material with a second packaging material applied on top of the cyclodextrin composition and cured after lamination to form a treated laminate; the laminate is tentered (oriented, or stretched) monoaxially or biaxially either before or after the cyclodextrin composition is cured. After cure and tentering, the treated laminate is formed into a bag or used as a wrap for a produce container. In yet another related example, the cured cyclodextrin composition is a pressure sensitive adhesive disposed on a packaging material; the pressure sensitive adhesive is affixed to a container to form a treated laminated container. The pressure sensitive adhesive is adhered to the interior or exterior side of the container to form a treated laminated container.

In some embodiments, the packaging material is directly applied to the produce, for example as a continuous or discontinuous coating, or as part of an adhesive or in printed characters on a printed or reverse printed produce label. In such embodiments, all or a portion of the coating or label contains the cyclodextrin composition. In some embodiments, an adhesive used to adhere a label on produce or on a package, or to seal a package, includes the cyclodextrin composition. The label is adhered to the interior or exterior of the package; that is, the surface contacting the interior of the enclosed volume, or the surface that does not contact the interior of the enclosed volume directly but only indirectly, e.g. via permeability of the packaging material to water and/or the olefinic inhibitor. Such constructions are embodiments of treated laminated containers. Treated laminated containers include those having a cured cyclodextrin composition is disposed between one surface of the container and a second layer of a packaging material that is the same or different from the first packaging material that is the packaging material from which the container is formed. In such embodiments, cyclodextrin composition is generally not in direct contact with the interior, enclosed volume of the container; that is, it is disposed between two layers of packaging material. Thus, the packaging material surface in contact with the produce and also in contact with the cured cyclodextrin composition must be permeable to water and the olefinic inhibitor in order for the olefinic inhibitor to be released from the cyclodextrin inclusion complex and into the interior volume of the container. In some such embodiments, the laminate structure is permeable to the olefinic inhibitor on a first side thereof and is impermeable to the olefinic inhibitor on a second side thereof; in some embodiments the container is a treated laminated container wherein the laminate structure is permeable to water on at least a first side thereof.

In some embodiments, the packaging material itself is permeable to the olefinic inhibitor. In some such embodiments, the cyclodextrin composition is coated on, or contacted to, the exterior of the package via lamination, and the olefinic inhibitor is released such that it diffuses through the package into the interior space where the produce is situated. In some such embodiments, the packaging material is also water permeable and the release of the olefinic inhibitor is controlled by water vapor permeating the packaging material from the interior of the enclosed volume; in other such embodiments, the packaging material is impermeable to water and release of the olefinic inhibitor is controlled by ambient humidity that exists exterior to the enclosed volume. In some embodiments, the packaging material is not permeable to the olefinic inhibitor. In such embodiments, the packaging material is a barrier that prevents the escape of the olefinic inhibitor from the enclosed space defining the produce package. In still other embodiments the packaging material itself is permeable to the olefinic inhibitor, but one or more surface treatments, coatings, or layers (in the case of a multilayer film or carton, for example) provide a barrier function.

In treated laminated containers, two different packaging materials are employed in some embodiments as the first and second packaging materials between which the cyclodextrin composition is sandwiched; as such, the packaging materials can be of differentiable permeability. Thus, for example, the interior-facing side of the laminate is permeable to the olefinic inhibitor but in some embodiments is impermeable to water, whereas the exterior facing side of the laminate is impermeable to the olefinic inhibitor and in some embodiments is permeable to water. In some such embodiments, a controlled humidity atmosphere provided outside the container—such as in a storage facility—is used to control the rate of release of the olefinic inhibitor, instead of the interior atmosphere within the container itself.

The cyclodextrin compositions are coated onto the surface of a packaging material, or directly onto produce, and cured. Coating is accomplished using any of the known coating technologies available in the industry wherein mixtures of curable monomers are coated prior to curing. In some embodiments coating is accomplished without employing elevated temperatures, that is, by employing ambient temperatures of a processing facility. In other embodiments, the temperature during coating and curing is between about 5° C. and 75° C., or between about 0° C. and 25° C. Useful coating techniques employed to coat the cyclodextrin compositions include, for example, die coating, curtain coating, flood coating, gap coating, notch bar coating, wrapped wire bar drawdown coating, dip coating, brush coating, spray coating, pattern coating such as rotogravure coating, and print coating employing printing technologies such as flexographic printing, inkjet printing, lithographic printing techniques, letterset printing, and screen printing. The viscosity profile of the cyclodextrin composition including properties such as shear thinning, the shape and composition of the packaging material or produce, and the desire to coat the entirety vs. a portion of a surface dictates which of the known coating technologies are useful to coat the cyclodextrin compositions. For example, die coating, notch bar coating, and the like are usefully employed to coat the entirety of a substantially planar web of packaging material, whereas in embodiments where only a portion of a surface is to be coated, or coating onto a formed container or onto produce is desirable, one or more spray, dip, or print coating technologies is desirably employed. Where only one specific portion of a packaging material is to be coated, print coating or in some embodiments rotogravure coating is desirably used. In some such embodiments, the print coating is embossed indicia.

Radiation curable inks, such as UV curable inkjet and flexographic inks, are known in the industry and such apparatuses to apply and cure such inks are easily obtained. Further, radiation curable ink formulations are easily modified to include the amount of the cyclodextrin inclusion complex necessary to accomplish delivery of the needed amount of complexed olefinic inhibitor to a surface of one or more packaging materials. Thus, in one embodiment of the invention, a UV curable inkjet ink is modified to include an amount of a cyclodextrin inclusion complex, for example by admixing the cyclodextrin inclusion complex into the ink; the modified inkjet ink is delivered over a target area to the packaging material and cured to provide a treated packaging material. Other printing techniques, for example flexographic printing, are also of utility in delivering a precise and reproducible amount of cyclodextrin inclusion complex to a packaging material by similarly incorporating the inclusion complexes containing the olefinic inhibitors. Large scale production of packaging will, in some embodiments, realize greater efficiency with flexographic printing instead of inkjet printing.

The desired thickness of the coated cyclodextrin composition layer is dictated by the amount of cyclodextrin inclusion complex in the cyclodextrin composition, the inherent equilibrium ratio of the cyclodextrin inclusion complex with uncomplexed olefin inhibitor, the permeability of the cured cyclodextrin composition to the olefinic inhibitor, the viscosity or coating thickness requirements of the technique employed to coat the cyclodextrin composition, the size of the portion of surface area containing the cured cyclodextrin composition, the type of produce to be packaged, and the volume of the enclosed space surrounding the produce. In sum, the coating thickness is selected to provide an amount of cyclodextrin inclusion complex that is effective to provide a suitable atmospheric (gaseous) concentration of the olefinic inhibitor to the enclosed space such that the useful life of the produce is extended. In some embodiments, an effective amount of olefinic inhibitor in the atmosphere within the enclosed space of the produce container is between about 2.5 parts per billion (ppb) to about 10 parts per million (ppm), or between about 25 ppb and 1 ppm. In various embodiments, the coating thickness is between about 0.001 micrometer (μm) and 10 millimeter (mm) thick, or between about 0.01 μm and 1 mm thick, or between about 0.1 μm and 0.5 mm thick, or between about 1 μm and 0.25 mm thick, or between about 2 μm and 0.1 mm thick.

Once the cyclodextrin composition is coated onto a packaging material, it is cured in situ to form a treated packaging material. In situ curing is accomplished without the need to employ elevated temperatures; however, in some embodiments elevated temperatures are suitably employed; the curing process is not particularly limited as to the temperature employed. For example, in embodiments, the temperature employed during cure of the cyclodextrin composition is about 0° C. to 135° C., or about 30° C. to 120° C., or between about 50° C. to 110° C. Maintaining both coating and curing temperatures at or below about 100° C. is easily accomplished. In embodiments where the cyclodextrin inclusion complex is 1-MCP complexed with α-cyclodextrin, elevated temperatures do not cause appreciable release of the olefinic inhibitor from the cyclodextrin inclusion complex.

In some embodiments, in situ curing is accomplished employing UV radiation. UV radiation is electromagnetic radiation having a wavelength of between 10 nm and 400 nm. In embodiments, wavelengths between about 100 nm and 400 nm are useful; in other embodiments wavelengths between about 200 nm and 380 nm are useful. Wavelength, as well as radiation intensity and time of exposure, is selected based on processing parameters such as the absorption characteristics of the photoinitiator employed, polymerization kinetics of the monomer(s) selected, and thickness of the cyclodextrin composition coating. Suitable photoinitiators and amounts thereof employed in the cyclodextrin compositions are described above. Useful methodologies and criteria to consider in UV curing are described, for example, in U.S. Pat. No. 4,181,752.

In embodiments, curing is accomplished in an environment that is substantially free of atmospheric moisture, air, or both. Such an environment is achieved, in some embodiments, by purging the coated area with an inert gas such as carbon dioxide or nitrogen during the curing. In other embodiments, most conveniently where the coated packaging material is a flat sheet or film, water and air are suitably excluded during cure by applying a UV-transparent, water impermeable liner on top of the coated, uncured cyclodextrin composition. The coated cyclodextrin composition is cured by irradiating through the liner; then the liner is removed e.g. to facilitate windup of the treated packaging film or sheet, wherein the film or sheet layers provide a suitable water barrier. In other embodiments the liner is left on top of the treated packaging material until it is employed as a treated container or treated package insert, at which point the liner is removed. The liner material is not particularly limited in composition or thickness and is selected for UV transparency at the desired wavelength. In embodiments, the liner is selected to have a sufficiently low level of adhesion to the cured cyclodextrin composition that the liner can be removed after cure without appreciable damage to the cured cyclodextrin composition. In some embodiments, the liner is added after cure to facilitate storage of the treated packaging material or treated container; in such cases, the liner does not need to be transparent to radiation but rather is selected primarily to exclude water.

In some embodiments, curing of the coated cyclodextrin composition is accomplished employing electron beam, or e-beam, radiation. In other embodiments, prepolymerization of the cyclodextrin composition is followed by coating onto a packaging material, and subjecting to e-beam radiation in order to crosslink the cyclodextrin composition. In some such embodiments, additional monomers, including monomers with more than one polymerizable moiety, are added to the prepolymerized cyclodextrin composition prior to coating and subjecting to e-beam radiation. E-beam methods employed to polymerize the cyclodextrin composition are described, for example, in the web article by Weiss et al., "*Pulsed Electron Beam Polymerization*", posted Jan. 1, 2006. Numerous methods of polymerization and/or crosslinking facilitated by e-beam are described in both patent and nonpatent literature. Some examples of methods useful to polymerize and/or crosslink the cyclodextrin compositions of the invention include, for example, U.S. Pat. Nos. 3,940,667; 3,943,103; 6,232,365; 6,271,127; 6,358,670; 7,569,160; 7,799,885, and the like.

E-beam is a high energy ionizing radiation that creates free radicals and is capable of penetrating materials that are opaque to UV radiation. As such, use of e-beam polymerization or crosslinking presents the possibility of grafting components of the cyclodextrin composition to the packaging material directly. Many of the packaging materials listed above, for example polyolefin, polyvinyl chloride, and polystyrene, are susceptible to e-beam radiation; that is, one or more free radicals are formed along the polymer backbone in some cases by e-beam irradiation. Free radical formation along the polymer backbone, in turn, presents an opportunity for the polymer backbone to bond to one or more components of the cyclodextrin composition. In embodiments, one or more monomers or cyclodextrin inclusion complexes are bonded, or grafted, to the packaging material by employing e-beam mediated polymerization or e-beam mediated crosslinking. The dose of radiation delivered is carefully adjusted in each case to avoid domination by the competing process of chain scission.

In the manufacture of the cyclodextrin compositions of the invention where the cyclodextrin composition comprises the cyclodextrin inclusion complex formed from 1-MCP and α-cyclodextrin (1-MCP/c/α-CD), we have found that careful control of water content during coating, curing, and subsequent storage prior to use is useful in maintaining the stability of the 1-MCP/c/α-CD complex. As water is reduced, the 1-MCP is more controllably maintained within the central pore of the α-cyclodextrin. Storage of treated packaging materials containing 1-MCP/c/α-CD is advantageously accomplished by either covering the treated portion of the treated packaging material with a liner that is impermeable to water vapor; or in the case of treated films or sheets formed from water vapor impervious thermoplastics, winding the films or sheets into rolls, or storing sheets or containers in stacks; or otherwise containing the treated packaging materials in a low humidity environment. In some embodiments, bulk quantities of treated packaging materials, such as rolls of treated packaging film or nested stacks of treated containers, are wrapped in water impervious plastic or foil wrappers or enclosed in water impermeable bags for storage and/or shipping.

In some embodiments, where a liner is applied over the cured cyclodextrin compositions, the liner includes one or more desiccants. In some such embodiments, the desiccants are embedded in, or adhered to, the liner. The desiccant is employed along with the liner itself to exclude water during storage and/or shipping. Examples of desiccants that are suitably employed include silica gel, activated charcoal, calcium sulfate, calcium chloride, montmorillonite clay, and molecular sieves. The desiccant is attached to the liner in such a manner that it remains substantially attached to the liner when the liner is removed from the treated packaging material or treated container.

In some embodiments, a treated packaging material or a treated laminate is stretched before or after curing the cyclodextrin composition. Monoaxial or biaxial stretching, or tentering, of thermoplastic film forming materials and laminates formed from such materials is carried out as an efficient and economical way to form thin films with enhanced strength. Where the cyclodextrin composition is applied to a thermoplastic film prior to tentering, a relatively thick coating and/or a high concentration of the cyclodextrin inclusion complex is employed because the layer containing the cyclodextrin inclusion complex is predictably made thinner at the prescribed stretch ratio.

3. Uses of the Compositions, Methods, and Articles

The treated packaging materials and treated containers are usefully employed in enclosing produce. The treated package inserts are usefully included within the enclosed volume of packaged produce. In embodiments, the treated packaging material, treated container, or treated package insert is arranged such that the cured cyclodextrin composition contacts the interior atmosphere of the enclosed volume surrounding one or more produce items, the enclosed volume being provided by the container. The type and conformation of the produce container is not particularly limited; any bag, box, punnet, tub, cup, pallet bag, transportation interior (e.g. truck interior), etc. that defines an enclosed space usefully employs the treated packaging materials, containers, and/or package inserts of the invention.

The surface area and thickness of the cured cyclodextrin composition exposed to the interior of a produce container is selected to provide a suitable atmospheric (gaseous) concentration of the olefinic inhibitor to the enclosed space such that the useful life of the produce is optimized. In many embodiments, optimum useful life of the produce means extended for the maximum amount of time possible. The optimum atmospheric concentration of the olefinic inhibitor is dictated by the type of produce to be packaged and the expected temperature of storage of the produce as well as the partial pressure of the olefinic inhibitor at the target temperature. Factors affecting the provision of the optimum atmospheric concentration of olefinic inhibitor include the amount of cyclodextrin inclusion complex in the cyclodextrin composition, the inherent equilibrium ratio of the cyclodextrin inclusion complex with uncomplexed olefin inhibitor, the permeability of the cured cyclodextrin composition to the olefinic inhibitor, the permeability of the packaging material to the olefinic inhibitor—that is, the expected loss ratio of the olefinic inhibitor to the exterior of the package or container—the viscosity or coating thickness requirements of the technique employed to coat the cyclodextrin composition, the volume of the enclosed space surrounding the produce, and the amount of water expected within the container as a result of initial amount added/enclosed and expected transpiration of the plant material. If the container is not completely sealed to the exterior atmosphere, for example if there are gaps or the packaging material itself has pores or holes, then any expected loss of released (gaseous) olefinic inhibitor must also be taken into account when calculating the amount of cyclodextrin composition to be disposed in the interior of the produce container.

In embodiments, the amount of olefinic inhibitor in the atmosphere that is required for a particular packaging application is estimated based on what produce is to be packaged and the known effective level of that inhibitor with respect to the specific produce material; then the coating thickness and area coated (that is, the total coating volume) is varied based on the enclosed volume, and concentration of the cyclodextrin inclusion complex included in the cured cyclodextrin composition. Other factors affecting olefinic inhibitor release from the cyclodextrin inclusion complex within a cured cyclodextrin composition of the invention include the presence and amount of humectants or desiccants within the package, water and 1-MCP permeability/adsorbability/absorbability of the cured cyclodextrin composition, water and 1-MCP permeability/adsorbability/absorbability of the packaging material, any controlled or modified atmosphere present within the package, and respiration rate of the targeted produce material. Further, the amount of water provided within the enclosed space, that is, the amount of water vapor vs. liquid water in the enclosed space at the target temperature, must also be considered.

In such calculations, the value of delivering a targeted coating amount to the targeted enclosed volume is realized. Certain embodiments described above are particularly advantageous in delivering a precisely measured amount of olefinic inhibitor to an enclosed volume, as well as enabling an easily varied amount of cyclodextrin composition to a target container. For example, inkjet printing is well understood to deliver precise and easily varied volumes of material to substrates over an easily varied volume. Further, UV curable inkjet inks are known in the industry and such apparatuses to apply and cure such inks are easily obtained. We have found that UV curable inkjet formulations are easily modified to include the small amount of the cyclodextrin inclusion complex necessary to accomplish delivery of the needed amount of olefinic inhibitor to a surface of one or more packaging materials. Thus, in one embodiment of the invention, a UV curable inkjet ink is modified to include an amount of a cyclodextrin inclusion complex, for example by admixing the cyclodextrin inclusion complex into the ink; in some such embodiments, the ink is dried with a desiccant to remove water before addition of the cyclodextrin inclusion complex. The modified inkjet ink thus obtained is delivered over a target area to the packaging material and cured to provide a treated packaging material. Other printing techniques, for example flexographic printing, are also of utility in delivering a precise and reproducible amount of cyclodextrin inclusion complex to a packaging material.

Another advantage of using printing techniques to deliver the cyclodextrin compositions of the invention is that printing is easily incorporated into a production assembly line setup. Further, ink is easily kept dry while in a tank awaiting printing on a production line. In this way, long term storage issues encountered in some applications, that is, the need to keep the cured cyclodextrin composition dry, is obviated. Yet another advantage of using printing techniques to apply the cyclodextrin compositions is the ability to employ reverse print labeling. In reverse print labeling, a transparent labelstock is printed with indicia on the side of the label that will contact the package, typically by virtue of an adhesive. Alphanumeric characters are thus printed in reverse, that is, as the mirror images thereof. When the label is applied to the package, the labelstock protects the printed indicia from wear and tear. In the current use, the cyclodextrin composition printed in reverse labeling mode is then disposed against the package or the produce. Reverse print labeling is also useful for printing onto what will become the interior of a transparent package, such that the printed indicia is directly exposed to the interior of the package.

In some embodiments, delivering a targeted coating amount to the targeted enclosed volume is realized by coating and curing a cyclodextrin composition on a flat web, then cutting the web into portions as treated package inserts. In some such embodiments, variable size treated package inserts are cut to provide different amounts of cyclodextrin inclusion complexes to address different produce requirements or different enclosed volumes. In other embodiments, uniform sections are cut and one, two, or more sections are included as treated package inserts in various packages depending on the type of produce and enclosed volume in each application. For example, in embodiments where the treated package insert is a label, one label is applied to each produce item and several produce items are included in a single enclosed space. Variable size containers holding a variable number of produce items is easily addressed in this manner.

In yet a different set of embodiments, the adhesive coated onto a label is employed on the outside of a package to provide a packaging material that is a laminated packaging material.

In some embodiments, the packaging material used to make the treated packaging materials of the invention and the treated packages and containers of the invention employ further means to control the amount of water (vapor and/or liquid) enclosed within the treated package while in the presence of the produce material. While the amount of water in a package's enclosed space is of concern from the standpoint of release of the olefinic inhibitor from the cured cyclodextrin compositions of the invention, it is well known that very high levels of moisture in a package containing produce material is also separately detrimental to certain moisture sensitive produce (berries, citrus, lettuce, mushrooms, onions, and peppers, for example). Excess moisture triggers various physiological disorders in some postharvest fruits and vegetables, shortening shelf life and quality. In particular, liquid water in the form of condensation on produce material surfaces hastens spoilage and considerably shortens storage life. In some embodiments, internal humidity controllers (humectants and desiccants) are incorporated into porous sachets, within the packaging material of the invention, or even within the cyclodextrin compositions themselves in conjunction with the treated packaging material of the invention. In embodiments, humidity controllers help maintain optimum in-package relative humidity (about 85% to 95% for cut fruits and vegetables), reduce moisture loss from the produce material itself, and/or prevent buildup of excess moisture in headspace and interstices where microorganisms can grow. The amount of 1-MCP incorporated within the packaging structure will be different in packaging having excess water as contrasted by lower humidity packaging of low transpiration postharvest products. Therefore, to operate the technology a number of factors (chemical and biological) will be considered to manufacture optimum packaging structures and bulk shipping containers for different groups of postharvest products.

The treated packaging materials of the invention are also useful in embodiments where modified atmosphere packaging (MAP), equilibrium modified atmosphere packaging (EMAP), or controlled atmosphere packaging (CAP) is employed. The objective in MAP is to provide a desired atmosphere around produce by providing a sealed container having controlled permeability to oxygen and carbon dioxide, resulting in an improvement in produce quality when compared to air storage. Typically, the permeability of the container changes with temperature and partial pressures of each gas exterior to the container. The objective in CAP is to displace some or all of the atmospheric air composition (78% $N_2$, 21% $O_2$) within the container with e.g. carbon dioxide or nitrogen or a blend of two or more gases in a desired proportion. A number of patents set forth various features of MAP and CAP. U.S. Pat. No. 7,601,374 discusses both approaches and also references a substantial list of other patents issued for various MAP and CAP technologies. It will be appreciated that the cured cyclodextrin compositions of the invention find further utility in conjunction with MAP, CAP, or technologies that combine features of both approaches.

MAP is a useful approach for maintaining improved flavored fruits and vegetables by minimizing development of off-flavors due to fermentative metabolism or odor transfer from fungi or other sources. MAP is recognized to improve resistance to postharvest stresses, decay and other plant disorders. An 'active package' having a modified atmosphere integrated with the controlled release of an olefinic inhibitor as delivered by the cyclodextrin compositions of the invention will improve the quality of fresh-cut fruits and vegetables for consumers including single-serve, ready-to-eat packaging and containers for vending machines. In an exemplary embodiment of the invention, MAP or CAP is used in conjunction with the treated packaging materials of the invention for large polyethylene bags employed to packaging pallets of cartons, wherein the cartons contain fresh produce. Such pallet-size bags are widely employed for shipment of pallets of produce, supported in cartons; the bags are employed for the purpose of enclosing the produce in a modified or controlled atmosphere during shipping. In some such embodiments, the bags, the paperboard (e.g. polyethylene extrusion coated paperboard) cartons, labels on the cartons or the bag, a treated insert, or a combination of two or more thereof include a treated packaging material of the invention.

EMAP is a method to help prolong the shelf life of fresh produce by optimizing the in-package equilibrium atmosphere. This is achieved by modifying the permeability of the packaging film. Film micro-perforation is one way to regulate the equilibrium concentrations of $O_2$ and $CO_2$. Micro-perforated films are apertured films or otherwise rendered porous, by puncturing or by stretching a film made from a mixture of a thermoplastic material and particulate filler. These films permit the transfer only by molecular gas/vapor diffusion and block the transfer of liquid. Examples of microporous or micro-perforated films include FRESHHOLD® film, available from River Ranch Technology, Inc. of Salinas, Calif.; P-PLUS® film, available from Sidlaw Packaging of Bristol, Great Britain and described in U.S. Pat. Nos. 6,296,923 and 5,832,699; and films from Clopay Plastic Products Co. of Mason, Ohio described in U.S. Pat. Nos. 7,629,042 and 6,092,761.

Additionally, in some embodiments of the invention, the gas permeability of non-perforated and nonporous films is modified by simply manufacturing films of different thicknesses or using the selectivity of hydrophilic films produced from segmented block copolymers, and employing these materials as packaging materials in conjunction with the cured cyclodextrin compositions. Segmented block copolymers or multi-block copolymers consist of alternating flexible soft segments and crystallizable rigid segments. The properties of segmented block copolymers are varied by changing the block lengths of the flexible (soft) and rigid segments. Rigid and flexible segments are thermodynamically immiscible and, therefore, phase separation occurs. The rigid segments crystallize and form lamellae in the continuous soft phase. Rigid segments can contain ester, urethane or amide groups, while the flexible segments are usually polyesters or polyethers-poly(ethylene oxide) (PEO) and/or more hydrophobic poly(tetramethylene oxide) (PTMO). In breathable film, the gas vapor is transported mainly through the soft phase; selective gas permeability depends on the density of the hydrophilic groups in the polymer, the relative humidity, and the temperature.

The treated packaging materials of the invention are also useful in embodiments where specialized and selectively permeable packaging materials are employed. One example of a selectively permeable packaging material is BreatheWay® packaging, currently used in conjunction with fresh-cut produce marketed by Apio, Inc. of Guadalupe, Calif. BreatheWay® films are selectively permeable membranes that control influx of oxygen and outflux of carbon dioxide in order to provide adjusted $O_2/CO_2$ ratios to extend shelf life. The membranes are also temperature responsive. While such packaging provides improved $O_2/CO_2$ ratios for extending shelf life of respiring produce, it does not otherwise inhibit ripening of the produce. Examples of other suitable breathable hydrophilic films include PEBAX®, a thermoplastic polyamide manufactured by Total Petrochemicals USA, Inc. of Houston, Tex.; SYMPATEX®, a breathable hydrophilic polyether-ester block copolymer manufactured by SympaTex Technologies GmbH of Unterföhring, Germany; HYTREL®, a thermoplastic polyester elastomer manufactured by DuPont deNemours and Co. of Wilmington, Del.; and segmented polyurethanes such as ELASTOLLAN® (ELASTOGRAN®) and PELLETHANE®, supplied by Dow Chemicals of Midland, Mich. These polymers have a large, selective gas permeability range. The cured cyclodextrin compositions of the invention, in conjunction with such permeable membrane technology, represent a complete solution to extended shelf life of respiring produce.

It will be appreciated that the end use articles and applications of the invention benefit in a number of ways from the advantages offered by the compositions and methods described herein. The cyclodextrin inclusion complexes are easily formed and isolated using mild conditions and high yields of inclusion complex formation are realized. The cyclodextrin inclusion complexes are easily stored until added to a cyclodextrin composition. The cyclodextrin compositions are easily formed, coated, and cured using mild conditions with generally small amounts of the cyclodextrin inclusion complex added to a curable and coatable or sprayable composition of easily varied viscosity. The cured cyclodextrin compositions are easily stored or can be formed and used in a production line. A variable and precise amount of cyclodextrin inclusion complex is easily and reproducibly added to produce packages. A variety of easily implemented methods of delivering the cured cyclodextrin compositions to produce packages and packaging materials is possible.

4. 1-Methylcyclopropene (1-MCP) as the Olefinic Inhibitor

In embodiments where 1-MCP is the olefinic inhibitor, the target concentration for many produce items is between about 2.5 ppb to about 10 ppm, or between about 25 ppb and 1 ppm. In embodiments the 1-MCP cyclodextrin inclusion complex is formed with α-cyclodextrin; that is, 1-MCP/c/α-CD. A factor in addition to those factors mentioned above affecting 1-MCP release from 1-MCP/c/α-CD is the amount of water contained in the enclosed space. This requires consideration of the amount of water provided within the enclosed space, amount of water released by respiring produce material, and the amount of water retained within the package as that amount changes with plant respiration.

In embodiments of the invention where the cyclodextrin inclusion complex 1-MCP/c/α-CD is employed in the cyclodextrin compositions, cured cyclodextrin compositions, treated packaging materials, and/or treated containers of the invention, produce is packaged in the enclosed volume defined by the container, and the treated packaging material is exposed to the interior atmosphere within the enclosed volume. Such exposure is, in various embodiments, either direct exposure of a cured coating within the interior atmosphere, or indirect exposure of such a coating applied to the exterior of a package, wherein the package is permeable to water, 1-MCP, or both. The enclosed volume includes an appropriate and activating amount of water such that the 1-MCP/c/α-CD releases the 1-MCP into the package interior at sufficient concentration to inhibit produce ripening or maturation. The 1-MCP is also released from the packaging material by exposing the packaging material to a controlled level of water vapor and/or liquid water. The release of 1-MCP from the cyclodextrin inclusion complex 1-MCP/c/α-CD facilitated by water vapor is explored and described in detail by Neoh, T. Z. et al., *Carbohydrate Research* 345 (2010), 2085-2089. In embodiments, the cured cyclodextrin composition is both permeable to the olefinic inhibitor and to water vapor to a sufficient degree to maintain a ripening or maturation inhibiting amount of olefinic inhibitor within the enclosed volume and in the presence of water vapor.

The researchers of Neoh, T. Z. et al., *Carbohydrate Research* 345 (2010), 2085-2089 studied dynamic complex dissociation of 1-MCP/c/α-CD and observed that increasing humidity generally triggered 1-MCP complex dissociation. However, the dissociation was greatly retarded at 80% relative humidity, presumably owing to collapse of the crystalline structure; then abrupt dissociation corresponding to complex dissolution was observed at 90% relative humidity. However, the researchers noted, as did the inventors in this instant invention, that even at 100% relative humidity that less than 20% of the complexed 1-MCP is released. In fact, an average of less than one-fifth (~17.6%) of the total amount of complexed 1-MCP was dissociated at the end of the experiments while ~83.4% 1-MCP remained complexed.

In some embodiments, during distribution and storage of the packaged produce, when storage temperature is between about 0° C. and 20° C., the relative humidity in the enclosed volume around the produce will be between about 50% and 100% due to normal water loss from produce respiration within the enclosed package volume. The increase in humidity within the enclosed volume of the package is sufficient, in embodiments, to release a portion of the 1-MCP from the 1-MCP/c/α-CD. In other embodiments, the internal humidity of the treated container is adjusted by the addition of water to the container prior to sealing to form the enclosed volume. In some such embodiments relative humidity within the enclosed volume is provided by adding moisture (water mist, spray or steam) to air by humidifiers during packaging or by controlling the humidity of the environment in the packaging location, within the package itself, or both.

Unexpectedly, the cured cyclodextrin compositions of the invention continue to release higher concentrations of olefinic inhibitor with increasing amounts of water, even as the amount of water in an enclosed space reaches, and exceeds, the amount necessary to result in 100% relative humidity given the volume of space and the temperature. So for example, in some embodiments, a package is formed from treated packaging material; live plant material is added, and the package is sealed. Initially, the package contains less than 100% relative humidity; as the plant material respires within the package, 100% relative humidity is reached. As the humidity increases, the amount of olefinic inhibitor present in the atmosphere within the package also increases. In some embodiments, the amount of water released by the plant material exceeds the amount constituting 100% relative humidity, such that liquid water is formed. In such embodiments, we have found that the amount of olefinic inhibitor released within the package continues to increase even though the amount of vapor phase water cannot be increased and only liquid water is released into the sealed package atmosphere. In our experiments, we have found that the levels of olefinic inhibitor released by the cured cyclodextrin compositions within an enclosed space continues to increase in a predictable fashion with increasing amounts of water added, regardless of whether the water is in the form of vapor or liquid.

The relationship between the amount of water in an enclosed space and the release of 1-MCP from 1-MCP/c/α-CD complex was very surprising when dissociation (release) of 1-MCP was measured as a function of water addition to the complex. Water solubility of α-CD is 14.5 grams/100 mL, or 14.5 wt-%, at typical ambient temperatures. As is reported in Control Example A in the Experimental section below, a significant excess of water beyond the amount required to completely dissolve α-CD was required to dissociate 100% of the 1-MCP from the complex. The relationship between amount of water present and 1-MCP dissociation from 1-MCP/c/α-CD has been demonstrated in a supplied complex alone, as well as in the cured cyclodextrin compositions of the invention. The importance of the relationship between water and 1-MCP dissociation is of utmost importance in employing the technology because:

1) the amount of 1-MCP is regulated in the atmosphere surrounding fruits and vegetables on a country-by-country basis; and
2) the benefit (i.e., shelf life extension) derived from 1-MCP differs with exposure concentration for various types of produce material (see, e.g. Blankenship, S. M. and Dole, J. M., *Postharvest Biology and Technology* 28 (2003), 1-25); further, adverse affects to some produce materials are possible with excessive 1-MCP treatment concentrations.

In two examples of country-by-country regulation at the time of this writing, the United States' Environmental Protection Agency (EPA) currently limits 1-MCP to a maximum of 1 ppm in air by authority of Section 408 of the Federal Food, Drug, and Cosmetic Act (FFDCA); and the European Commission Health and Consumer Protection Directorate and Member States of the European Food Safety Authority similarly regulates 1-MCP under its various directives, limiting 1-MCP levels to amounts ranging from 2.5 ppb v/v to 1 ppm v/v.

Thus, in embodiments, 1-MCP dissociation must be carefully managed within the package headspace by controlling both the total amount of 1-MCP incorporated within the packaging structure and the release of 1-MCP from the inclusion complex. Additionally, in embodiments, the amount of residual water inherently adsorbable or absorbable by the cured cyclodextrin compositions of the invention further affects 1-MCP dissociation. In embodiments, the hydrophilic nature of the cyclodextrin itself increases the compatibility of water with a cured cyclodextrin composition into which a cyclodextrin inclusion complex is incorporated.

In embodiments of the invention where the cyclodextrin inclusion complex employed in the treated packaging materials of the invention is 1-MCP/c/α-CD, the amount of 1-MCP in the atmosphere that is required for a particular packaging application is calculated based on several factors; then the coating thickness and area coated (that is, the total coating volume) is varied based on the enclosed volume, concentration of 1-MCP/c/α-CD included in the cured cyclodextrin composition, and approximate fraction of 1-MCP/c/α-CD that is complexed (vs. uncomplexed α-CD) to arrive at the targeted atmosphere. Factors that must be considered in such a calculation include any humectants or desiccants within the package, water and 1-MCP permeability/adsorbability/absorbability of the cured cyclodextrin complex, water and 1-MCP permeability/adsorbability/absorbability of the packaging material, any controlled or modified atmosphere present within the package, and respiration rate of the targeted produce material. For example, if an atmosphere containing 1 ppm of 1-MCP is required and the targeted enclosed volume is 1 liter, then assuming 100% complexation and an overall density of the cured cyclodextrin composition of 1 g/cm$^3$, a cured cyclodextrin composition containing 1.71 wt % α-cyclodextrin coated 12.7 μm thick in an area totaling 2 cm$^2$ would provide the targeted 1 ppm of 1-MCP to the enclosed volume in the presence of water vapor using Ideal Gas Law conversion. In embodiments, the targeted weight range of 1-MCP/c/α-CD is 25 micrograms to 1 milligram per 1 liter of enclosed volume. In such calculations, the value of delivering a targeted coating amount to the targeted enclosed volume is realized. Certain embodiments described above are particularly advantageous in delivering a precisely measured amount of 1-MCP to an enclosed volume, as well as enabling an easily varied amount of cyclodextrin composition to a target container. For example, in some embodiments, inkjet printing is well understood to deliver precise and easily varied volumes of material to substrates over an easily varied volume. In other embodiments, addition of the inclusion complex to an adhesive formulation onto a label, followed by cutting a precise size label to apply to a packaging material, results in delivery of a precise amount of 1-MCP/c/α-CD to the treated packaging material.

EXPERIMENTAL SECTION

Example 1

A cyclodextrin inclusion complex is formed from α-cyclodextrin and 1-methyl cyclopropene (1-MCP) using the technique described by Neoh, T. L. et al., J. Agric. Food Chem. 2007, 55, 11020-11026 *"Kinetics of Molecular Encapsulation of 1-Methylcyclopropene into α-Cyclodextrin."* The inclusion complex is termed "1-MCP/c/α-CD." A 500 mL bottle is charged with 97.0 g of isobornyl acrylate, 1.0 g of hexanediol diacrylate, 1.0 g of 1-MCP/c/α-CD, and 1.0 g of 1-hydroxycyclohexyl benzophenone (IRGACURE® 184, obtained from Ciba Specialty Chemicals Corp. of Tarrytown, N.Y.). The bottle is firmly capped and the components are mixed by shaking the bottle briefly by hand.

About 2 mL of the mixture is removed with a metered dropper and dispensed on an 8.5 inch by 11 inch PET film and drawn down using a metering rod (Mayer rod) having a delivered coating thickness of 25 microns. Then the coated PET film is placed on a flat surface approximately 5 cm beneath a medium pressure mercury arc lamp operating at 200 watts per inch (79 watts per cm). After 30 seconds under the lamp, the film is removed. A silicone coated PET sheet (about 50 microns thick) is placed over the cured coating and allowed to sit on a laboratory bench overnight.

A die cutter is used to cut a 1 cm by 1 cm square of the coated portion of the sheet. The liner is removed from the coated square and the coated square placed a 250 mL serum bottle. The bottle is then sealed with a TEFLON® faced silicone septa. Headspace concentrations of 1-MCP are measured after 1 hour following introduction of the coated square into bottle. The 1-MCP headspace concentration is quantified using gas chromatography by removing 1 mL of gas from the sample bottle using a gas sampling valve interfaced directly to a GC column having FID detector. No measurable concentration of 1-MCP is detected because of the lack of humidity in the headspace of the jar.

Then 50 μl of deionized water is injected into the jar. Care is taken so that the liquid water does not directly contact the coated square. The sealed jar is allowed to sit on the lab bench for one hour after the injection of water, then a second headspace sample is analyzed. A final headspace sample is analyzed 24 hours after the injection of water. At 1 hour after injection of the water, 0.5 ppm of 1-MCP is measured in the headspace. After 24 hours, 0.5 ppm of 1-MCP is measured in the headspace.

Example 2

An inclusion complex of 1-butene and α-cyclodextrin was formed using the technique described by Neoh, T. L. et al., J. Agric. Food Chem. 2007, 55, 11020-11026 *"Kinetics of Molecular Encapsulation of 1-Methylcyclopropene into*

α-*Cyclodextrin*" except that 1-butene (99.0% pure, Scott Specialty Gases, Plumsteadville, Pa.) was bubbled through a saturated α-cyclodextrin solution instead of 1-MCP. A precipitate was formed during the process, which was collected by filtering through a 10 micron fitted filter, and dried at ambient temperature at 0.1 mm Hg for about 24 hours. The inclusion complex was termed "1-butene/c/α-CD."

1-butene/c/α-CD was analyzed by adding 100 mg of the collected and dried precipitate to a 250 mL glass bottle equipped with a septum cap, taking care to ensure that no powder adheres to the walls of the bottle. After about 1 hour, 250 μL of headspace gas was removed from the bottle using a six port, two-position gas sampling valve (Valco #EC6W) interfaced directly to a gas chromatograph (GC; Hewlett Packard 5890) using a RTx-5 GC column, 30 m×0.25 mm I.D., 0.25 μm film (obtained from Restek, Inc., of Bellefonte, Pa.) and equipped with flame ionization detector (FID). No measurable concentration of 1-butene was detected because of the lack of humidity (water vapor) in the headspace of the bottle. Then 3 mL of water was injected into the bottle through the septum, and the bottle is placed on a mechanical shaker and mixed vigorously for about 1 hour. After the shaking, 250 μL of the headspace gas is removed and added to an empty 250 mL bottle equipped with a septum cap, wherein the interior of the bottle was purged with nitrogen gas. The headspace concentration of 1-butene was quantified in the second bottle using gas chromatography by removing 250 μL of gas from the 250 mL bottle using a six port, two-position gas sampling valve (Valco #EC6W) interfaced directly to a GC column having FID detector previously calibrated with a 6-point 1-butene (99.0% pure, Scott Specialty Gases, Plumsteadville, Pa.) calibration curve. Employing this method, the yield of complexed 1-butene/c/α-CD was found to be 72.5%.

A 20 mL bottle was charged with 9.8 g of UV Coating VP 10169/60 MF-2NE (obtained from Verga GmbH of Aschau am Inn, Germany) and 0.2 g of 1-butene/c/α-CD. The bottle was firmly capped and the components were mixed by shaking the bottle by hand until uniformly dispersed.

About 3 mL of the mixture was removed with a dropper dispensed on a glass pan. A rubber ink roller was used to spread the mixture on the glass and roller. Next, the roller was used to coat the mixture on the coated side of a 20 cm by 20 cm section of polyethylene extrusion coated paper (REYNOLDS® Freezer Paper, 90 microns total thickness). The roller delivered a coating nominal thickness of 0.3 microns. A razor blade was used to cut a 5 cm by 10 cm rectangle from the coated sheet. Then the coated cut rectangle was passed by hand about 10 cm beneath a medium pressure mercury arc lamp operating at 200 watts per inch (79 watts per cm). After 1.5 seconds exposure to the lamp, the cured rectangle was removed. The cured rectangle was allowed to sit on a laboratory bench overnight coating side down.

Six replicate coated rectangles were made in this fashion. Each rectangle was placed in a 250 mL serum bottle. Then the six bottles were sealed with TEFLON® faced silicone septa. The 1-butene headspace concentration was quantified using gas chromatography by removing 250 μL of gas from the sample bottle using a six port, two-position gas sampling valve interfaced directly to the GC column having FID detector. No measurable concentration of 1-butene was detected in the bottle headspace.

Then 50 μL of deionized water was injected into each bottle. Care was taken so that the liquid water did not directly contact the coated rectangles. The headspace of each of the six sealed bottles was analyzed at 0.5, 1, 2, 4, 8, 24, and 96 hours after the injection of water wherein about 3 mL of the 250 mL bottle headspace volume was removed for each analysis. In each sampling, the amount of 1-butene released from the UV coated rectangles was quantified by gas chromatography against a 6-point 1-butene calibration curve having a 0.998 correlation coefficient. Table 1 and FIG. 1 illustrate the average of six replicate samples of 1-butene headspace concentration and standard deviation.

TABLE 1

Headspace concentration of 1-butene according to the procedure of Example 2.

| Hours | 1-Butene Ave. ppm (v/v) | Stdev (ppm) |
|---|---|---|
| 0.5 | 0.46 | 0.24 |
| 1 | 1.5 | 0.55 |
| 2 | 3.0 | 0.61 |
| 4 | 4.9 | 0.78 |
| 8 | 6.0 | 0.35 |
| 24 | 7.6 | 1.6 |
| 96 | 7.8 | 1.7 |

Example 3

A 20 mL bottle was charged with 9.6 g of UV Coating VP 10169/60 MF-2NE (obtained from Verga GmbH of Aschau am Inn, Germany). Then 0.4 g of 1-MCP/α-cyclodextrin complex (4.7% 1-MCP obtained from AgroFresh of Spring House, Pa.) termed "1-MCP/c/α-CD" was added to the bottle. The bottle was then firmly capped and shaken by hand by hand until the blends appear uniformly dispersed, resulting in a 4.0 wt-% 1-MCP/c/α-CD blend. Three additional blends containing 2.0 wt-%, 1.0 wt-% and 0.5 wt-% of 1-MCP/c/α-CD were prepared in the same manner.

A rubber ink roller was used to deliver a thin (nominally 0.3 μm) coating to a 20 cm by 20 cm polyethylene extrusion coated paper sheet using the technique of Example 2.

Figure 2:
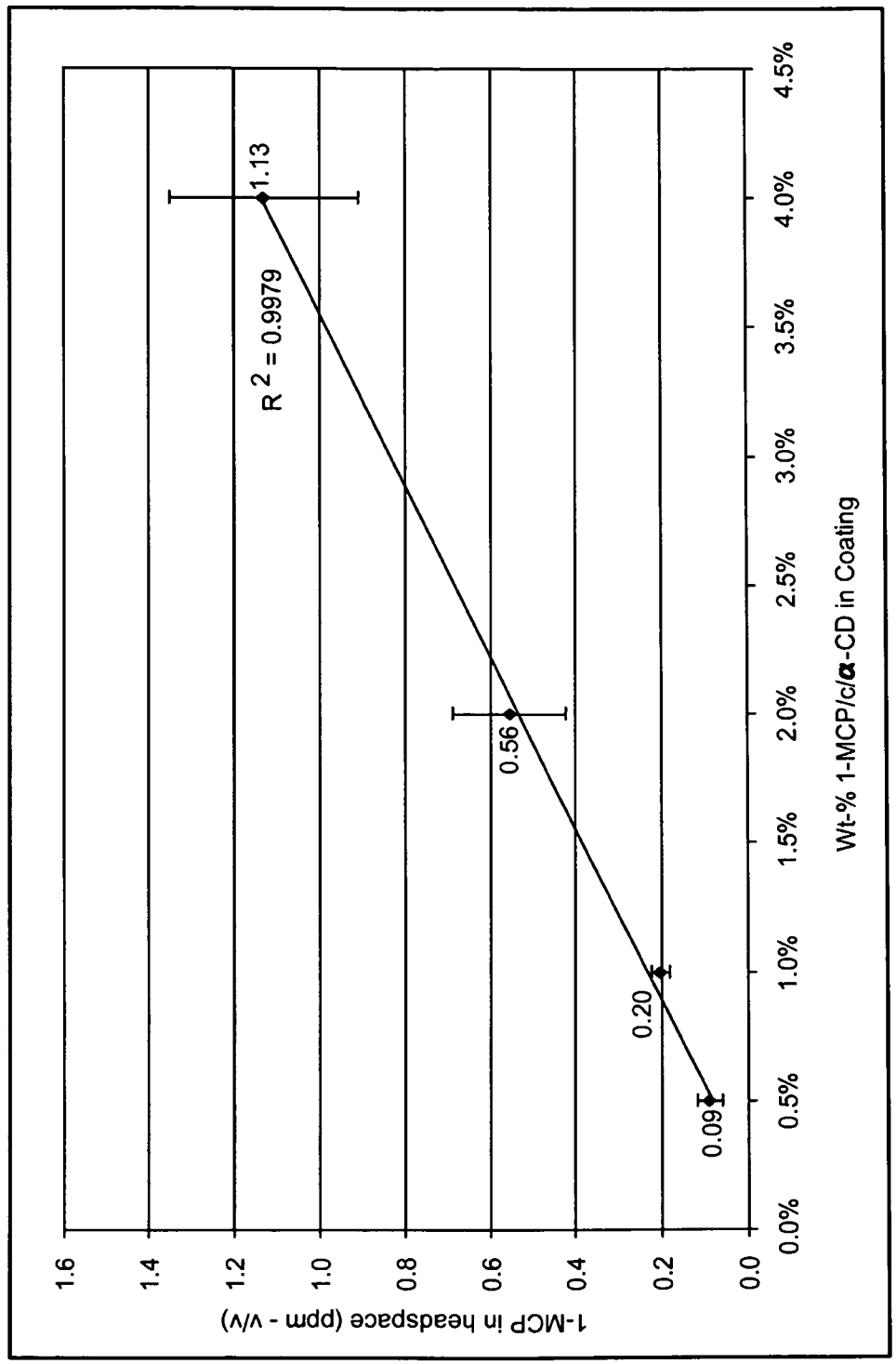
FIG. 2 illustrates headspace concentration of 1-MCP as a function of coating composition.

Using razor blade, 2.5 cm×10 cm rectangles were cut from the coated portion of each of the sheets. Then the coated rectangular sheets were cured using the procedure of Example 2. Each cured, coated rectangle was placed in a 250 mL serum bottle. The bottle was then sealed with TEFLON® faced silicone septa. Then 20 μL of deionized water was injected into each bottle. Care was taken so that the liquid water did not directly contact the coated rectangles. Headspace was analyzed for 1-MCP 24 hours after the injection of water, using the technique employed in Example 2, and employing the 6-point 1-butene calibration curve as described in Example 2. Table 2 and FIG. 2 give the 24-hour average 1-MCP headspace concentration and standard deviation for each of the coated and cured rectangular sheets. These data illustrate that 1-MCP was released into the headspace in a linear manner (0.99 correlation coefficient) with increasing wt-% 1-MCP/c/α-CD in the coating when exposed to water vapor (humidity).

TABLE 2

Headspace concentration of 1-MCP according to the procedure of Example 3.

| Wt-% 1-MCP/c/α-CD | 1-MCP Ave. ppm (v/v) | Stdev (ppm) |
|---|---|---|
| 0.5 | 0.09 | 0.03 |
| 1 | 0.20 | 0.02 |
| 2 | 0.56 | 0.13 |
| 4 | 1.1 | 0.22 |

Example 4

A 4.0 wt-% 1-MCP/c/α-CD blend was made according to the technique of Example 3. A rubber ink roller was used to deliver a coating having a nominal thickness of 0.3 μm to a 20 cm by 20 cm polyethylene extrusion coated paper sheet using the technique of Example 2. The coated sheet was cured according to the procedure of Example 2.

Figure 3:
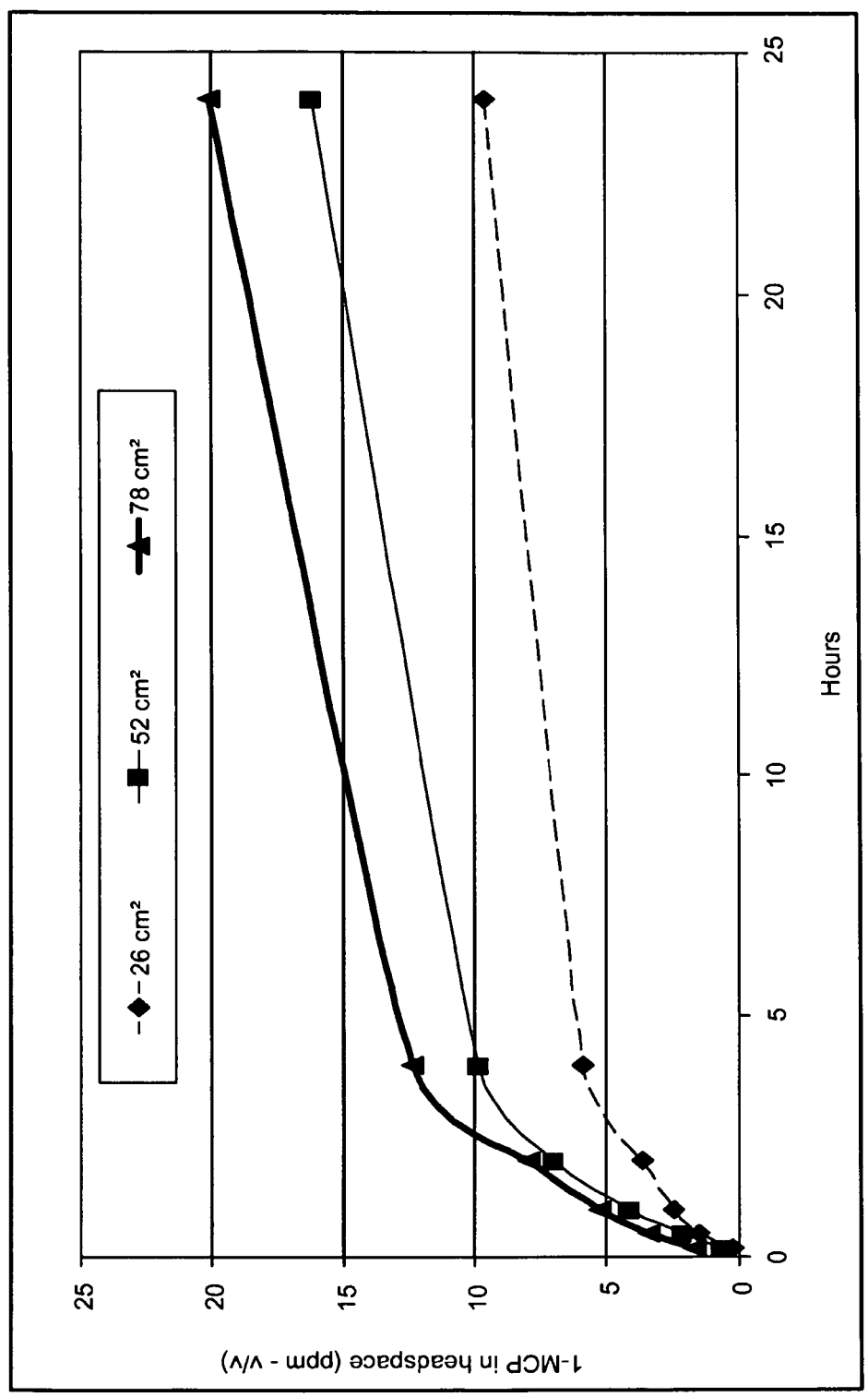
FIG. 3 illustrates headspace concentration of 1-MCP as a function of time, varying surface area coated.

Using a razor blade, 26 cm², 52 cm², and 78 cm² samples were cut from the coated portion of the sheet. Each sample was placed in a 250 mL serum bottle. The bottles were sealed with TEFLON® faced silicone septa. Then 204 of deionized water was injected into each bottle. Care was taken so that the liquid water did not directly contact the test sample. Bottle headspace analysis was conducted according to the technique of Example 3 at 0.17 hours, 0.5 hours, 1 hour, 2 hours, 4 hours and 24 hours after the injection of water. 1-MCP headspace concentrations as a function of test sample area and times are provided in Table 3 and FIG. 3. These data illustrate that 1-MCP was released into the headspace in a in a predictable manner over time with increasing coated surface area having 4.0 wt-%1-MCP/c/α-CD when the coating is exposed to water vapor (humidity).

TABLE 3

Headspace concentration of 1-MCP according to the procedure of Example 4.

| Time Hrs | 26 cm² 1-MCP (ppm – v/v) | 52 cm² 1-MCP (ppm – v/v) | 78 cm² 1-MCP (ppm – v/v) |
| --- | --- | --- | --- |
| 0.17 | 0.25 | 0.66 | 1.7 |
| 0.5 | 1.5 | 2.2 | 3.4 |
| 1 | 2.4 | 4.2 | 5.2 |
| 2 | 3.7 | 7.0 | 7.9 |
| 4 | 5.8 | 9.9 | 12.4 |
| 24 | 9.6 | 16.1 | 20.0 |

Example 5

Figure 4:
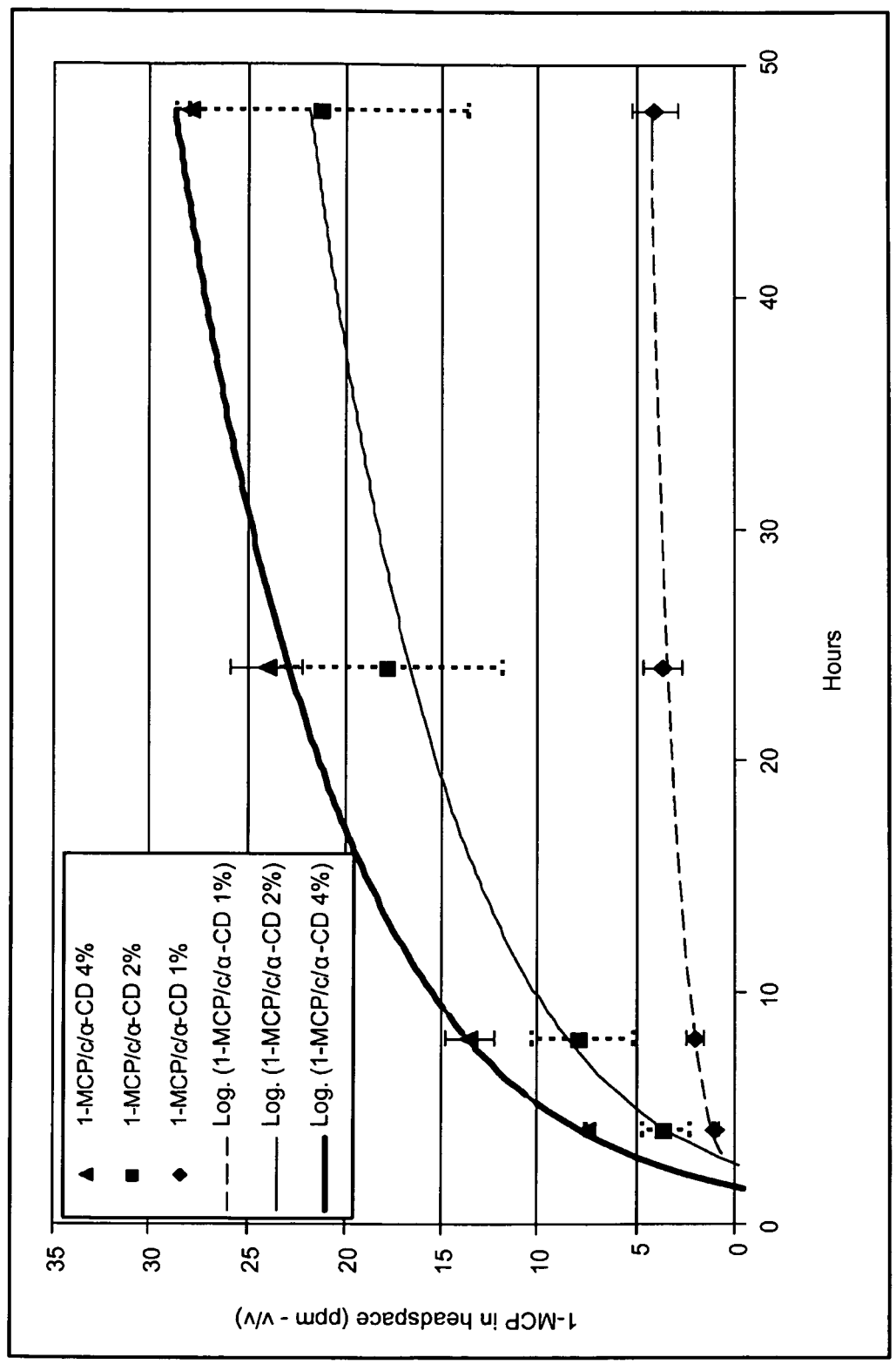
FIG. 4 illustrates headspace concentration 1-MCP as a function of time, varying coating composition.

Using a razor blade, six 5 cm×10 cm rectangles were cut from the coated portions of 20 cm by 20 cm sheets prepared as in Example 3 and having 1.0 wt-%, 2.0 wt-% and 4.0 wt-% 1-MCP/c/α-CD, and the coated rectangles were cured according to the technique of Example 2. The rectangles were individually placed in 250 mL serum bottles. The bottles were sealed with TEFLON® faced silicone septa. Then 20 μL of deionized water was injected into each bottle. Care was taken so that the liquid water did not directly contact the test sample. Bottle headspace was analyzed at 4, 8, 24 and 48 hours after the injection of water, using the technique of Example 3. The results are provided in Table 4 and FIG. 4 and give the average headspace concentration and standard deviation for the different wt-% 1-MCP/c/α-CD coatings as a function of time. These data illustrate that 1-MCP was released into the headspace in a in a predictable manner over time with increasing wt-% 1-MCP/c/α-CD in the coating when exposed to water vapor (humidity).

TABLE 4

Headspace concentration of 1-MCP according to the procedure of Example 5.

| Wt- % 1-MCP/c/α-CD, coated | Hours | 1-MCP (ppm – v/v) in Headspace | Stdev |
| --- | --- | --- | --- |
| 1 | 4 | 0.96 | 0.15 |
| 1 | 8 | 2.0 | 0.44 |
| 1 | 24 | 3.6 | 0.98 |
| 1 | 48 | 4.0 | 1.2 |
| 2 | 4 | 3.5 | 1.2 |
| 2 | 8 | 7.8 | 2.6 |
| 2 | 24 | 17.8 | 5.9 |
| 2 | 48 | 21.2 | 7.5 |
| 4 | 4 | 7.5 | 0.08 |
| 4 | 8 | 13.5 | 1.3 |
| 4 | 24 | 24.0 | 1.8 |
| 4 | 48 | 28.0 | 0.05 |

Example 6

A 100 mL quartz beaker was charged with 54 g of 2-isooctyl acrylate, 6 g of acrylic acid, and 0.60 g of 1-hydroxycyclohexyl phenyl ketone (IRGACURE® 184, Ciba Specialty Chemicals Corp. of Tarrytown, N.Y.). The beaker was equipped with a mechanical stirrer, and the contents were mixed for about 5 minutes while sparging with dry helium. Then the beaker was irradiated with a medium pressure mercury arc lamp operating at 79 watts per cm situated about 15 cm from the side of the beaker. The light was turned off when the contents of the flask were of a honey-like consistency, about 1.5 minutes. The beaker was further charged with 3.23 g of 1-MCP/c/α-CD, 0.89 g of IRGACURE® 184, 5.8 g of isooctyl acrylate, and 0.72 g of acrylic acid. The beaker contents were mixed until uniformly dispersed, about 5 minutes.

About 4 mL of the mixture in the bottle was removed with a metered dropper and dispensed on 30.5 cm by 30.5 cm white paper labelstock, and drawn down using a metering rod (Meyer coating rod #30) having a delivered coating thickness of 25 microns. Then a 21.5 cm by 28 cm silicone coated polyester (PET) film sheet (120 μm thick (obtained from the 3M Company of St. Paul, Minn.) was placed over the coated labelstock, taking care not to entrain air bubbles. The coated and covered labelstock was cut into 10 cm by 20 cm rectangles using a paper cutter. The cut samples were passed by hand about 15 cm beneath a medium pressure mercury arc lamp operating at 79 watts per cm; multiple hand passes beneath the UV light or about 30 seconds under the lamp was used to cure the adhesive. The cured coated labelstock sheets were allowed to sit PET side up on a laboratory bench overnight.

A paper cutter was used to cut six replicate 2.5 cm by 2.5 cm squares from the sheets. Because the UV cured coating composition is a pressure sensitive adhesive, or PSA, the 2.5 cm by 2.5 cm squares are termed "PSA labels." Each PSA label, with the silicone coated PET still in place, was placed in a 250 mL serum bottle. Each bottle was sealed with a TEFLON® faced silicone septum. The headspace concentration of 1-MCP was measured after 1 hour following introduction of the PSA label into a bottle, using the technique of Example 3 except that 250 μL of gas was removed from the sample bottle for the analysis. 1-MCP was below the quantification limit of 0.01 ppm.

Then 50 μL of deionized water was injected into each bottle. Care was taken so that the liquid water did not directly contact the labels. The sealed bottle headspace was analyzed at 10 minutes, 30 minutes, and 60 minutes, using the technique of Example 3. A final headspace sample was analyzed 16 hours after the injection of water. These data are shown in Table 5. The data illustrate that 1-MCP was released from a PSA label into the headspace when exposed to water vapor (humidity) and that its concentration increases over time.

TABLE 5

Headspace concentration of 1-MCP according to the procedure of Example 6.

| Hours | 1-MCP ppm (v/v) Average | Stdev |
|---|---|---|
| 0.17 | 0.01 | 0.01 |
| 0.5 | 1.3 | 0.84 |
| 1 | 3.6 | 0.75 |
| 16 | 29.7 | 8.0 |

Example 7

This method is designed to measure the permeability of 1-MCP through polyethylene film into a confined, fixed volume headspace following release from a PSA label adhered to the surface of the film defining the fixed volume. The methodology simulates the headspace of a flexible film package having initially low relative humidity, wherein a PSA label containing 1-MCP is adhered to the outside of the package. As the humidity rises inside the package by respiration of fresh agricultural products, the water vapor increases in concentration and it diffuses through the package film to the outside environment but also into the PSA. Thus, as the water vapor diffuses through the film into the 1-MCP adhesive label adhered to the outside of the package film; 1-MCP released from the label adhesive into the fixed volume (headspace) was measured.

A coated, cured labelstock sheet made according to the procedure of Example 6 was cut by hand into an 11 cm diameter circle. Next the PET liner was removed from the label and the label was adhered via the PSA to a 13.5 cm diameter, 1 mil (25 µm) thick polyethylene (PE) film (obtained from the Pliant Corporation of Schaumburg, Ill.). The paper side of this structure was then covered with aluminum foil. The foil/paper/PSA/PE layered structure was mounted onto the open end of a 1,000 mL glass reaction kettle bottom (6947-1LBO, from Corning Glass of Corning, N.Y.) and sealed to the kettle's glass flange using aluminum sealing rings. The layered structure was oriented over the 11 cm opening with the PE film facing in and the aluminum facing out. The glass reaction kettle was modified with a silicone septum port to allow sampling of the 1,000 mL headspace. Headspace analysis was conducted by removing 250 µL of headspace volume from the 1,000 mL glass kettle and analyzing according to the technique of Example 3.

Two hours after the film and label were sealed to the flange of the reaction kettle bottom and without any added water inside the 1,000 mL volume; an initial headspace analysis was conducted and revealed no detectible levels of 1-MCP (<0.01 ppm). Then 200 µL of water was added through the septum port to the inside of the glass kettle. The headspace was analyzed for 1-MCP at 17, 25 and 90 hours after the injection of water using the technique employed in Example 3. At 17 hours, 25 hours, and 90 hours after injection of the water, the 1-MCP headspace concentration was 3.6 ppm, 7.0 ppm and 8.0 ppm of 1-MCP, respectively. These results demonstrate a PSA coated label containing 1-MCP and adhered to a vapor permeable film surface can release 1-MCP to the inside package headspace following the introduction of water vapor inside the package headspace.

Control Example A

Water solubility of α-CD is 14.5 grams/100 mL, or 14.5 wt-%, at typical ambient temperatures (Szejtli, J. (1988), Cyclodextrin Technology, Kluwer Academic Publishers, page 12). A sample of 1-MCP/c/α-CD powder was obtained (AgroFresh of Spring House, Pa.). According to the supplier's specification sheet, 1-MCP was 4.7 wt % of α-CD or 88.7 wt % 1-MCP complex based on a theoretical 1:1 molar ratio of 1-MCP to α-CD; this corresponds to a resulting headspace concentration of 8,600 ppm. A series of tests were conducted to measure the dissociation of 1-MCP from the supplied 1-MCP/c/α-CD as a function of added water. First, 0.1 g aliquots of the supplied 1-MCP/c/α-CD powder were added to each of 5, 250 mL bottles, which were then capped with TEFLON® faced septa. Varying amounts of water were added to the bottles by syringe, and then the bottles were mechanically shaken for one hour, followed by headspace measurement for 1-MCP according to the procedure of Example 3. The amounts of water added per 0.1 g of the supplied 1-MCP/c/α-CD complex, and the resulting headspace measurements after 1 hour at about 20 C, are shown in Table 6.

Our test results showed a 5.8 wt % 1-MCP or 111 wt % 1-MCP/c/α-CD complex (greater than 1:1 complex) resulting in a headspace concentration of 10,610 ppm. At 1.0 grams of water per 0.10 grams 1-MCP/c/α-CD, α-CD water solubility was exceeded yet 1-MCP was only 66% dissociated. A polynomial regression was used to calculate the dissociation at 100% RH in the headspace for the five samples of Table 6 (i.e., 4.3 milligrams water per 250 mL volume, see Example 8 for source and calculation of this information). The calculated amount of dissociated 1-MCP at 100% RH was 18 wt-%.

These results were surprising since a significant excess of water beyond the amount required to completely dissolve α-CD (14.5 grams/100 mL, as reported above) was required to dissociate 100% of the complexed 1-MCP.

TABLE 6

Headspace concentration of 1-MCP according to the procedure of Control Example A.

| $H_2O$, g | 1-MCP, ppm (v/v) |
|---|---|
| 0.25 | 3,050 |
| 0.5 | 4,750 |
| 1.0 | 6,850 |
| 2.0 | 9,850 |
| 3.0 | 10,610 |

Example 8

A 4.0 wt-% 1-MCP/c/α-CD coating blend was made according to the technique of Example 3. A 20 cm by 20 cm polyethylene extrusion coated paper sheet was coated with the mixture using the technique of Example 2. A paper cutter was used to cut nine, 5 cm by 10 cm rectangles from the sheet. The cut, coated rectangles were passed by hand about 10 cm beneath a medium pressure mercury arc lamp operating at 79 watts per cm. After 1.5 seconds exposure to the lamp, the sample was removed. The cured sample was allowed to sit on a laboratory bench overnight coating side down.

Each cured sample was placed in a 250 mL serum bottle. Each bottle was sealed with a TEFLON® faced silicone septum. The amount of liquid water that would, in vapor form, correspond to 100% relative humidity (RH) at 20° C. is 17.3 g/m³, or 17.3 g per 1000 L. The density of water at 20° C. is 0.9982 g/mL. Thus, at 20° C., 4.3 µL of liquid water added to an enclosed volume of 250 mL and containing no other water will vaporize to give 100% RH. Our laboratory facility temperature was 20° C.±5° C.

Figure 5:
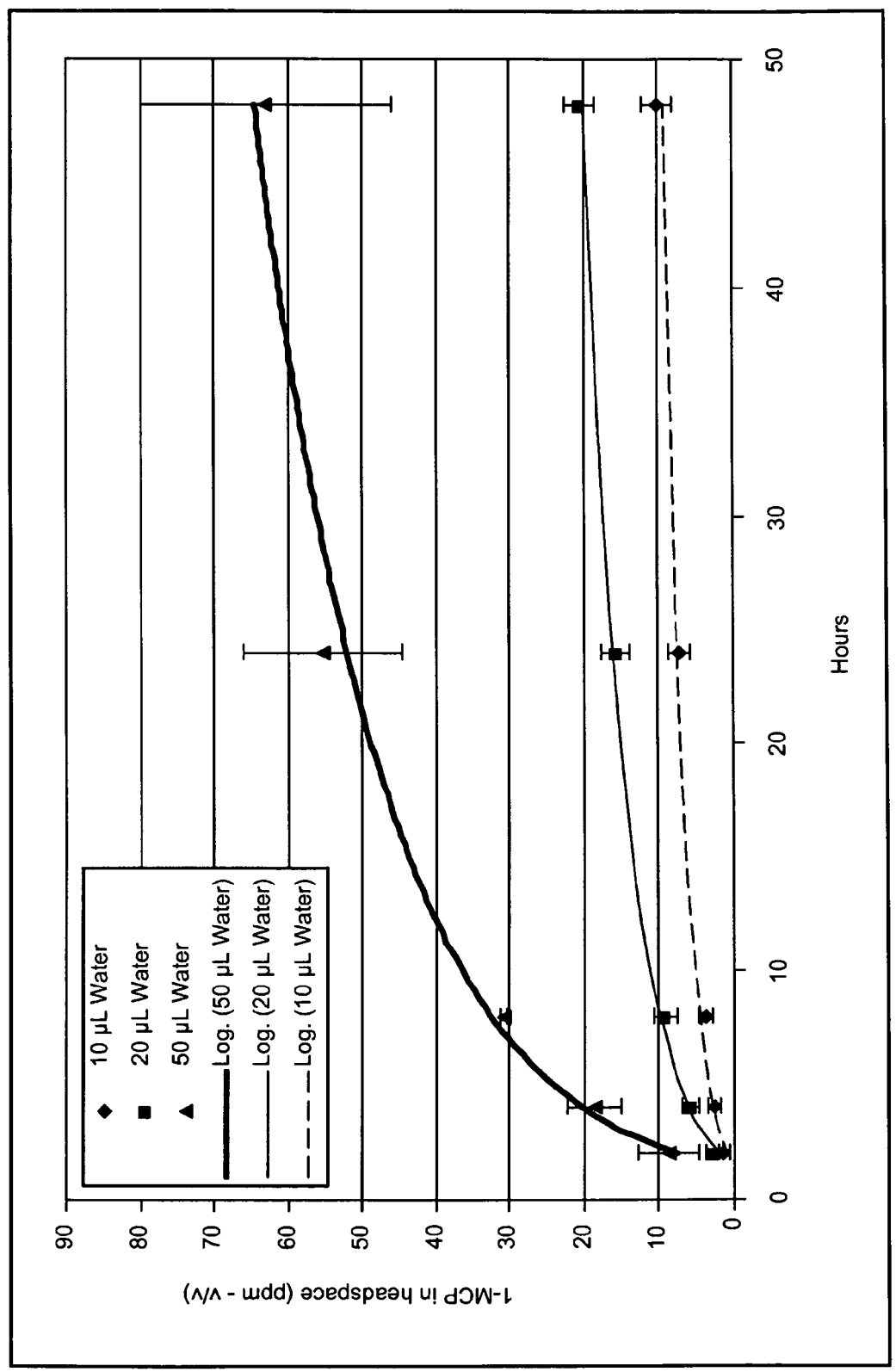
FIG. 5 illustrates headspace concentration of 1-MCP as a function of time, in the presence of varying amounts of liquid water.

Three of the bottles were injected with 10 µL of deionized water, three with 20 µL of deionized water, and three with 50 µL of deionized water. Care was taken so that the liquid water did not directly contact the coated square. The headspace of each bottle was analyzed for 1-MCP at 2 hours, 4 hours, 8 hours, 24 hours, and 48 hours after the injection of water, wherein the headspace analysis was conducted using the analytical technique employed in Example 3. The results of average headspace concentration and standard deviation are provided in Table 7 and FIG. 5.

TABLE 7

Headspace concentration of 1-MCP according to the procedure of Example 8.

| $H_2O$, µL | Time, hr | 1-MCP, average ppm (v/v) | Stdev |
|---|---|---|---|
| 10 | 2 | 1.3 | 0.77 |
| 10 | 4 | 2.5 | 0.81 |
| 10 | 8 | 3.8 | 0.94 |
| 10 | 24 | 7.1 | 1.5 |
| 10 | 48 | 10.0 | 2.0 |
| 20 | 2 | 2.6 | 1.1 |
| 20 | 4 | 5.8 | 1.3 |
| 20 | 8 | 9.2 | 1.7 |
| 20 | 24 | 15.7 | 1.9 |
| 20 | 48 | 20.5 | 2.0 |
| 50 | 2 | 8.7 | 4.1 |
| 50 | 4 | 18.6 | 3.6 |
| 50 | 8 | 30.8 | 0.42 |
| 50 | 24 | 55.3 | 10.7 |
| 50 | 48 | 63.0 | 17.0 |

Example 9

UV curable ink designed for thermal inkjet cartridges and industrial printing was formulated with 1-MCP/c/α-CD and printed onto film to demonstrate how UV ink can be incorporated into a flexible-package structure to release 1-MCP. ImTech UVBLK Series 912 cartridges were obtained from ImTech Inc. of Corvallis, Oreg. About 40 g of black ink was removed from the cartridge in which the ink was supplied. The ink was dried overnight in a closed container with 3A molecular sieves to remove residual water contained in the ink. Then 17.5 g of the dried ink was transferred to a 70 mL roller mill jar filled with 50 g of 3 mm glass beads to which 0.875 g of 1-MCP/c/α-CD was added to the UV ink. The jar was sealed and rotated on a roller mill at 140 rpm for four hours. At the end of four hours of rolling to disperse the 1-MCP/c/α-CD, an additional 4.375 g of dry UV ink was added making a 4 wt-% 1-MCP/c/α-CD containing ink. Then the ink was decanted from the glass beads.

A rubber ink roller was used to coat a discontinuous, thin (nominally 3 µm), but uniform UV ink coating onto a 10 cm by 20 cm section of PET film (120 microns thick, obtained from the 3M Company of St. Paul, Minn.) in the manner described in Example 2. UV ink coated rectangles were passed by hand about 10 cm beneath a medium pressure mercury arc lamp operating at 79 watts per cm for 1.5 seconds exposure to the lamp. The cured sample was allowed to sit on a laboratory bench overnight ink side down.

A paper cutter was used to cut two samples, 20 cm² and 81 cm², from the cured ink coated PET film sheet. The samples were individually placed in 250 mL serum bottles. The bottles were then sealed with TEFLON® faced silicone septa. Then 200 of deionized water was injected into the bottle. Care was taken so that the liquid water did not directly contact the ink coated PET film. After the injection of water into the bottle, 1-MCP was measured in the headspace using the analytical technique employed in Example 3. The test results are tabulated in Table 8; the results demonstrate 1-MCP release from the UV ink. The results further demonstrate that the 1-MCP releases slowly, increasing the bottle headspace concentration with increasing time.

TABLE 8

Headspace concentration of 1-MCP according to the procedure of Example 9.

| Hours | 20 cm² 1-MCP ppm (v/v) | 81 cm² 1-MCP ppm (v/v) |
|---|---|---|
| 0.17 | ND | ND |
| 0.5 | <0.01 | <0.01 |
| 1 | <0.01 | 0.05 |
| 2 | 0.01 | 0.18 |
| 4 | 0.04 | — |
| 8 | 0.05 | — |
| 21 | — | 0.51 |
| 27 | 0.09 | — |
| 48 | — | 0.60 |
| 170 | 0.76 | — |

Example 10

The ink containing 4 wt-% 1-MCP/c/α-CD from Example 9 was loaded back into the previously emptied cartridge. After refilling the cartridge, it was installed into a HP Inkjet 1600C printer (obtained from the Hewlett-Packard Company of Palo Alto, Calif.) and the calibration or head cleaning function was run. A medium density, black cross-hatch pattern obtained from Microsoft EXCEL software program 2003 (obtained from the Microsoft Corporation of Redman, Wash.) was used to format the entire printable page. The EXCEL pattern image was printed onto 3M, CG3460 Transparency Film (polyester film 120 microns thick for HP inkjet printers; obtained from the 3M Company of St. Paul, Minn.) using the dried, milled ink containing 4 wt-% 1-MCP/c/α-CD of Example 9. Immediately after printing, the printed side of the transparency film was overlaid with a 25 µm polyethylene film and then passed by hand about 10 cm beneath a medium pressure mercury arc lamp operating at 79 watts per cm for 3 seconds exposure to the lamp, with the polyethylene side facing the lamp. The methodology simulates a multilayer flexible-package where the inner surface of an outer, transparent, layer of the multilayer flexible material was printed (referred to as reverse printing). The printed surface was then laminated to other layers. The outside layer itself serves to protect the ink from abuse.

The following technique was designed to measure the permeability of 1-MCP, which was released from the reverse inkjet printed 3M Transparency Film, through PE film as the "inner layer" of a multilayer produce package. In a multilayer produce package, as the humidity rises inside the package by respiration of fresh agricultural products, the water vapor reaches a concentration that allows it to diffuse to the outside of the package. In this example, water also diffuses through the ink layer containing 1-MCP/c/α-CD. The reverse printed ink on the PET film releases 1-MCP which diffuses through the PE film into the interior of package (headspace) under a gradient of low 1-MCP concentration inside the bottle headspace and high 1-MCP concentration within the multilayer structure.

Using a paper cutter, a 5.5 cm by 16 cm rectangle (88 cm$^2$) was cut from the multilayer structure of the printed, cured ink on the PET sheet overlaid with PE. The rectangle was placed in a 250 mL serum bottle. The bottle was then sealed with a TEFLON® faced silicone septa. Then 100 µL of deionized water was injected into the bottle. Care was taken so that the liquid water did not directly contact the test sample. Bottle headspace was analyzed at 0.17, 0.5, 1, 2, 4, and 24 hours after the injection of water using the technique employed in Example 3. The results in Table 8 illustrate 1-MCP headspace concentration as a function of time for the "multilayer" film.

A second piece of PET transparency film was printed as in Example 9 except that the transparency film was not covered with PE film; the printed ImTech UVBLK Series 912 ink was cured on the PET film surface using a medium pressure mercury arc lamp operating at 79 watts per cm in the same manner as for Example 9. Then, using a paper cutter, a 1.2 cm by 16 cm rectangle (19 cm$^2$) was cut from the sheet. The rectangle was placed in 250 mL serum bottle. The bottle was then sealed with a TEFLON® faced silicone septa. Then 100 µL of deionized water was injected into the bottle. Care was taken so that the liquid water did not directly contact the test sample. Bottle headspace was analyzed at 0.17, 0.5, 1, 2, 4, and 24 hours after the injection of water using the technique employed in Example 3. The headspace concentration of 1-MCP as a function of time is also reported in Table 9 for the "monolayer" film.

TABLE 9

Headspace concentration of 1-MCP according to the procedure of Example 10.

| Hours | 88 cm$^2$ Multilayer 1-MCP ppm (v/v) | 19 cm$^2$ Monolayer 1-MCP ppm (v/v) |
|---|---|---|
| 0.17 | 0.25 | 0.50 |
| 0.5 | 0.46 | 0.52 |
| 1 | 1.1 | 0.50 |
| 2 | 1.5 | 0.51 |
| 4 | 3.2 | 0.52 |
| 24 | 8.3 | 0.49 |

Example 11

Polyethylene extrusion coated paperboard is one of the most commonly used fresh produce packaging materials. Typically, the paperboard is recyclable and has a thin (generally 30 µm or less) layer of polyethylene on one side or both sides. The extrusion coated surface can be coated or printed with a UV curable coating containing 1-MCP.

A 20 mL bottle was charged with 9.6 g of UV curable coating formulation (VP 10169/60 MF-2NE, obtained from Verga GmbH of Aschau am Inn, Germany). Then 0.4 g of 1-MCP/c/α-CD (4.7% 1-MCP, obtained from AgroFresh of School House, Pa.) was added to the bottle. The bottle was firmly capped and the components mixed by shaking the bottle by hand until the contents appeared to be uniformly dispersed, providing a UV curable mixture.

A polyethylene coated paperboard was prepared by heat laminating a 30 µm thick polyethylene film to a 20 cm×20 cm section of 600 µm thick solid bleached sulfate (SBS) paperboard (obtained from Graphic Packaging International of _) using a heated vacuum press. A rubber ink roller was used to deliver a thin (nominally 0.3 µm) coating of the UV curable mixture to the laboratory prepared polyethylene coated paperboard, using the technique of Example 2. A paper cutter was used to cut a 20 cm by 10 cm rectangle of the coated portion of the board. The coated rectangle was passed by hand about 10 cm beneath a medium pressure mercury arc lamp operating at 79 watts per cm. After 1.5 seconds exposure to the lamp, the sample was removed. The cured sample was allowed to sit on a laboratory bench overnight, coating side down.

After curing, 5 cm by 5 cm sections were cut from the 20 cm by 10 cm rectangles. Each section was individually placed into a 250 mL jar (tall clear WM SEPTA-JAR™, Fisher Scientific P/N 05-719-452; obtained from Fisher Scientific of Waltham, Mass.) equipped with a TEFLON™ faced septum (Fisher Scientific P/N 14-965-84). Each jar was injected with 200 µL of deionized water. Care was taken so that the liquid water did not directly contact the coated square. Jar headspace was analyzed for 1-MCP at five time periods (0.17, 0.5, 1, 2, 4 and 7 hours) after the injection of water, using the analytical technique employed in Example 3. The average headspace concentration of 1-MCP and standard deviation are tabulated in Table 10. The results exemplify that greater amounts of 1-MCP were released into the headspace from the UV coated substrate with increasing time.

TABLE 10

Headspace concentration of 1-MCP according to the procedure of Example 11.

| Hours | 1-MCP ppm (v/v) | Stdev |
|---|---|---|
| 0.17 | 0.16 | 0.09 |
| 0.5 | 0.63 | 0.40 |
| 1 | 1.6 | 0.67 |
| 2 | 3.6 | 1.5 |
| 4 | 7.3 | 2.5 |
| 7 | 12.5 | 2.8 |

Representative Embodiments

We now recite certain representative embodiments of the invention. The invention is not limited to these embodiments and other embodiments described above are also embodiments of the invention, or are embodiments of the invention when combined with any combination of the embodiments described below.

Embodiment 1

Embodiment 1 is suitably an embodiment of the invention either alone or when further combined with any additional limitation or element as described either above or in the following list. Embodiment 1 can be combined with a combination of two or more additional limitations or elements described above or in the following list. The following list contains limitations or elements that are intended to be combined in any manner with Embodiment 1 as further aspects of the invention, including in combination with any one or more other limitations or elements described above.

Embodiment 1 of the invention is a cyclodextrin composition comprising one or more radiation polymerizable monomers and a cyclodextrin inclusion complex, the cyclodextrin inclusion complex comprising a cyclodextrin compound and an olefinic inhibitor of an ethylene generation in produce, the olefinic inhibitor comprising a compound having the structure

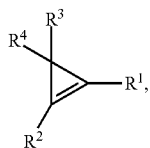

wherein each of $R^1$, $R^2$ are independently hydrogen or a $C_{1-16}$ hydrocarbyl group and $R^3$ and $R^4$ are independently hydrogen or a $C_{1-16}$ hydrocarbyl group with the proviso that at least one of $R^1$ or $R^2$ is methyl.

The list of additional limitations or elements includes, but is not limited to, the following:
  a. the one or more radiation polymerizable monomers comprise acrylic acid, methacrylic acid, an acrylate ester, a methacrylate ester, an acrylamide, a diacrylate, a triacrylate, a tetraacrylate, or a mixture thereof;
  b. the acrylate or methacrylate ester is an ester of an alcohol having between 1 and 18 carbons and is a linear, branched, or cyclic ester;
  c. the composition further comprises a photoinitiator;
  d. the composition further comprises one or more prepolymers;
  e. the cyclodextrin comprises a cyclodextrin derivative;
  f. the cyclodextrin inclusion complex contains about 0.1 to 0.99 mole of olefinic inhibitor per mole of cyclodextrin;
  g. the olefinic inhibitor comprises 1-methyl cyclopropene;
  h. the cyclodextrin comprises α-cyclodextrin;
  i. the cyclodextrin inclusion complex contains about 0.80 to 0.99 mole of 1-methyl cyclopropene per mole of α-cyclodextrin;
  j. the composition comprises between 0.01 wt % and 10 wt % of the cyclodextrin inclusion complex based on the weight of the composition;
  k. the composition is coatable;
  l. the composition is printable;
  m. the composition is an ink;
  n. the composition is a UV curable ink;
  o. the composition further comprises one or more colorants;
  p. the composition further comprises one or more adhesion promoters, antifouling agents, thermal stabilizers, oxidative stabilizers, water scavengers, adjuvants, plasticizers, or a combination of two or more thereof;
  q. the composition further comprises one or more desiccants;
  r. the composition further comprises one or more desiccants comprising silica gel, molecular sieves, or a combination thereof.

Embodiment 2

Embodiment 2 is suitably an embodiment of the invention either alone or when further combined with any additional limitation or element as described either above or in the following list. Embodiment 2 can be combined with a combination of two or more additional limitations or elements described above or in the following list. The following list contains limitations or elements that are intended to be combined in any manner with Embodiment 2 as further aspects of the invention, including in combination with any one or more other limitations or elements described above.

Embodiment 2 of the invention is a treated packaging material comprising a packaging material and a cured cyclodextrin composition disposed on at least a portion of one surface of the packaging material, the cured cyclodextrin composition comprising a polymer derived from one or more radiation polymerizable monomers and a cyclodextrin inclusion complex, the cyclodextrin inclusion complex comprising cyclodextrin and an olefinic inhibitor of an ethylene generation in produce, the olefinic inhibitor comprising a compound having the structure

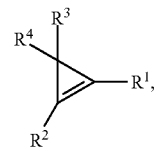

wherein each of $R^1$, $R^2$ are independently hydrogen or a $C_{1-16}$ hydrocarbyl group and $R^3$ and $R^4$ are independently hydrogen or a $C_{1-16}$ hydrocarbyl group with the proviso that at least one of $R^1$ or $R^2$ is methyl.

The list of additional limitations or elements includes, but is not limited to, the following:
  a. the treated packaging material comprises a film, a sheet, a foil, a bag, a punnett, a dish, a cup, a cover, a label, paperboard, a paperboard carton, or a treated package insert;
  b. the packaging material comprises a polyolefin or a polyester;
  c. the surface comprises a plasma treated surface;
  d. the treated packaging material further comprises a primer disposed between the packaging material and the cured cyclodextrin composition
  e. the cured cyclodextrin composition is permeable to water and to the olefinic inhibitor;
  f. the cured cyclodextrin composition has differential permeability to water and the olefinic inhibitor;
  g. the treated packaging material comprises a film, a sheet, a treated package insert, or a label and further comprising a liner disposed on top of the cured cyclodextrin composition;
  h. the liner is transparent to UV light;
  i. the liner is a foil;
  j. the liner further comprises one or more desiccants;
  k. the liner is preferentially removable at the interface of the liner and the cured cyclodextrin composition;
  l. the liner is impermeable to water;
  m. the packaging material is impermeable to water;
  n. the packaging material is impermeable to the olefinic inhibitor;
  o. the packaging material is permeable to water, permeable to the olefinic inhibitor, or permeable to both water and the olefinic inhibitor
  p. the packaging material is a selectively permeable membrane;
  q. the cured cyclodextrin composition comprises a pressure sensitive adhesive;
  r. the cured cyclodextrin composition is present as a coating on the packaging material;
  s. the coating is about 0.01 micron to 1 millimeter thick;
  t. the coating comprises printed indicia;
  u. the cured cyclodextrin composition is bonded to the packaging material;
  v. the packaging material comprises a treated laminate;

w. the packaging material comprises a treated laminate that is permeable to the olefinic inhibitor on a first side thereof and is impermeable to the olefinic inhibitor on a second side thereof;

x. the packaging material comprises a treated laminate that is permeable to water on at least a first side thereof;

y. the treated packaging material is tentered.

Embodiment 3

Embodiment 3 is suitably an embodiment of the invention either alone or when further combined with any additional limitation or element as described either above or in the following list. Embodiment 3 can be combined with a combination of two or more additional limitations or elements described above or in the following list. The following list contains limitations or elements that are intended to be combined in any manner with Embodiment 3 as further aspects of the invention, including in combination with any one or more other limitations or elements described above.

Embodiment 3 of the invention is a container comprising a treated packaging material, wherein the container comprises an enclosed volume, the treated packaging material comprising a cured cyclodextrin composition disposed on at least a portion of a surface of a packaging material, the cured cyclodextrin composition comprising a polymer derived from one or more radiation polymerizable monomers and a cyclodextrin inclusion complex, the cyclodextrin inclusion complex comprising an olefinic inhibitor of an ethylene generation in produce, the olefinic inhibitor comprising a compound having the structure

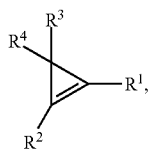

wherein each of $R^1$, $R^2$ are independently hydrogen or a $C_{1-16}$ hydrocarbyl group and $R^3$ and $R^4$ are independently hydrogen or a $C_{1-16}$ hydrocarbyl group with the proviso that at least one of $R^1$ or $R^2$ is methyl.

The list of additional limitation or elements includes, but is not limited to, the following:

a. the container is a bag, a punnett, a dish, a cup, or a paperboard carton;

b. the cured cyclodextrin composition is present as a coating on at least a portion of an interior surface of the container;

c. the cured cyclodextrin composition is present as a coating on at least a portion of an exterior surface of the container;

d. the cured cyclodextrin composition is present as a coating on a package insert;

e. the container is a treated laminated container;

f. the container is a treated laminated container wherein the laminate structure is permeable to the olefinic inhibitor on a first side thereof and is impermeable to the olefinic inhibitor on a second side thereof;

g. the container is a treated laminated container wherein the laminate structure is permeable to water on at least a first side thereof;

h. the container further comprises a desiccant;

i. the container further comprises an item of produce;

j. the enclosed volume comprises between 50% relative humidity and 100% relative humidity at a temperature between about 0° C. and 20° C.;

k. the enclosed volume comprises 100% relative humidity at a temperature between about 0° C. and 20° C. and further comprises liquid water;

l. the container comprises a modified atmosphere package;

m. the container comprises a controlled atmosphere package;

n. the container comprises a selectively permeable membrane;

o. the olefinic inhibitor is present in the enclosed volume at a concentration of about 2.5 parts per billion to 10 parts per million;

p. the olefinic inhibitor is present in the enclosed volume at a concentration of about 25 parts per billion to 1 part per million.

Embodiment 4

Embodiment 4 is suitably an embodiment of the invention either alone or when further combined with any additional limitation or element as described either above or in the following list. Embodiment 4 can be combined with a combination of two or more additional limitations or elements described above or in the following list. The following list contains limitations or elements that are intended to be combined in any manner with Embodiment 4 as further aspects of the invention, including in combination with any one or more other limitations or elements described above.

Embodiment 4 of the invention is a method of making a treated packaging material, the method comprising forming a cyclodextrin composition comprising one or more radiation polymerizable monomers and about 0.05 wt % to 10 wt % of a cyclodextrin inclusion complex based on the weight of the cyclodextrin composition, the cyclodextrin inclusion complex comprising cyclodextrin and an olefinic inhibitor of an ethylene generation in produce, the olefinic inhibitor comprising a compound having the structure

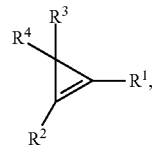

wherein each of $R^1$, $R^2$ are independently hydrogen or a $C_{1-16}$ hydrocarbyl group and $R^3$ and $R^4$ are independently hydrogen or a $C_{1-16}$ hydrocarbyl group with the proviso that at least one of $R^1$ or $R^2$ is methyl;

disposing the cyclodextrin composition onto at least a portion of one surface of a packaging material at a thickness of about 0.01 micron to 1 millimeter to form a coating; and exposing the coating to a source of radiation to form a cured cyclodextrin composition.

The list of additional limitations or elements includes, but is not limited to, the following:

a. the cyclodextrin composition further comprises about 0.1 wt % to 5 wt % of one or more photoinitiators based on the weight of the composition, wherein the irradiating is accomplished with UV radiation;

b. the cyclodextrin composition further comprises about 0.1 wt % to 5 wt % of one or more photoinitiators based on the weight of the composition; and further comprising an additional exposing of the cyclodextrin composition to a source of radiation prior to coating, wherein the source of radiation is ultraviolet radiation;

c. one or more additional monomers, an additional photoinitiator, or a combination thereof is added to the cyclodextrin composition after the additional exposing and before the disposing;
d. the source of radiation is electron beam radiation;
e. the source of radiation is ultraviolet radiation;
f. the coating is disposed over the entirety of one major surface of the packaging material;
g. the coating is disposed on a portion of one major surface of the packaging material;
h. the disposing is accomplished by printing;
i. the printing is gravure printing, flexographic printing, or inkjet printing;
j. the cured cyclodextrin composition comprises a pressure sensitive adhesive;
k. a liner is disposed over the cyclodextrin composition;
l. the liner is disposed prior to irradiating;
m. the liner is disposed after irradiating;
n. the liner comprises a desiccant;
o. the treated packaging material is a treated container;
p. the method further comprises forming a treated container from the treated packaging material;
q. the method further comprises forming a treated package insert from the treated packaging material;
r. the method further comprises forming a treated label from the treated packaging material;
s. the method further comprises forming a treated laminate;
t. the method further comprises forming a treated laminated container;
u. the method further comprises disposing the cured cyclodextrin composition inside a container having an enclosed volume, wherein the cured cyclodextrin composition contacts the enclosed volume;
v. the method further comprises disposing the cured cyclodextrin composition on the outside of a container having an enclosed volume, wherein the cured cyclodextrin composition is not in direct contact with the enclosed volume;
w. the method further comprises enclosing an item of produce inside the container.

The foregoing discloses embodiments of the invention. In the description and claims, "about" modifying, for example, the quantity of an ingredient in a composition, concentration, volume, process temperature, process time, yield, flow rate, pressure, and like values, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. "Optional" or "optionally" means that the subsequently described event or circumstance may but need not occur, and that the description includes instances where the event or circumstance occurs and instances in which it does not. The present invention may suitably comprise, consist of, or consist essentially of, any of the disclosed or recited elements. Thus, the invention illustratively disclosed herein can be suitably practiced in the absence of any element which is not specifically disclosed herein. The use of the singular typically includes and at least does not exclude the plural.

The specification, figures, examples and data provide a detailed explanation of the invention as it has been developed to date. The invention, however, can take the form of other embodiments without departing from the spirit or the intended scope of the invention. The invention therefore resides in the appended claims.

The invention claimed is:

1. A cyclodextrin composition comprising one or more radiation polymerizable monomers, a photoinitiator and a cyclodextrin inclusion complex, the cyclodextrin inclusion complex comprising a cyclodextrin compound and an olefinic inhibitor of an ethylene generation in produce, the olefinic inhibitor comprising a compound having the structure

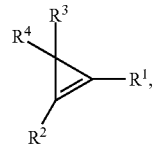

wherein each of $R^1$, $R^2$ are independently hydrogen or a $C_{1-16}$ hydrocarbyl group and $R^3$ and $R^4$ are independently hydrogen or a $C_{1-16}$ hydrocarbyl group with the proviso that at least one of $R^1$ or $R^2$ is methyl.

2. The composition of claim 1 wherein the one or more radiation polymerizable monomers comprise acrylic acid, methacrylic acid, an acrylate ester, a methacrylate ester, an acrylamide, a diacrylate, a triacrylate, a tetraacrylate, or a mixture thereof.

3. The composition of claim 1 wherein the composition further comprises one or more prepolymers.

4. The composition of claim 1 wherein the olefinic inhibitor comprises 1-methyl cyclopropene.

5. The composition of claim 4 wherein the cyclodextrin compound comprises α-cyclodextrin.

6. The composition of claim 1 wherein the composition comprises about 0.01 wt % to 10 wt % of the cyclodextrin inclusion complex based on the weight of the composition.

7. A method of making a cured cyclodextrin composition, the method comprising
a. forming a cyclodextrin composition comprising one or more radiation polymerizable monomers, a photoinitiator and about 0.05 wt % to 10 wt % of a cyclodextrin inclusion complex based on the weight of the cyclodextrin composition, the cyclodextrin inclusion complex comprising cyclodextrin and an olefinic inhibitor of an ethylene generation in produce, the olefinic inhibitor comprising a compound having the structure

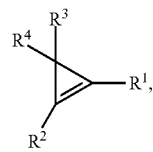

wherein each of $R^1$, $R^2$ are independently hydrogen or a $C_{1-16}$ hydrocarbyl group and $R^3$ and $R^4$ are independently hydrogen or a $C_{1-16}$ hydrocarbyl group with the proviso that at least one of $R^1$ or $R^2$ is methyl;
- b. disposing the cyclodextrin composition onto at least a portion of one surface of a packaging material at a thickness of about 0.01 micron to 1 millimeter to form a coating; and
- c. exposing the coating to a source of radiation to form a cured cyclodextrin composition.

8. The method of claim 7 wherein the cyclodextrin composition comprises about 0.1 wt % to 5 wt % of one or more photoinitiators based on the weight of the composition, wherein the source of radiation is ultraviolet radiation.

9. The method of claim 7 wherein the cyclodextrin composition comprises about 0.1 wt % to 5 wt % of one or more photoinitiators based on the weight of the composition; and further comprising exposing the cyclodextrin composition to ultraviolet radiation prior to the disposing.

* * * * *